United States Patent [19]
Theodore et al.

[11] Patent Number: 5,985,826
[45] Date of Patent: Nov. 16, 1999

[54] METHODS OF USING HEPATIC-DIRECTED COMPOUNDS IN PRETARGETING STRATEGIES

[75] Inventors: Louis J. Theodore, Lynnwood; Donald B. Axworthy; John M. Reno, both of Brier, all of Wash.

[73] Assignee: NeoRx Corporation, Seattle, Wash.

[21] Appl. No.: 08/808,024

[22] Filed: Mar. 3, 1997

Related U.S. Application Data

[62] Division of application No. 08/351,651, Dec. 7, 1994.

[51] Int. Cl.$^6$ ........................ A61K 31/70; A61K 31/715; A61K 31/73; A61K 38/14
[52] U.S. Cl. .................................. 514/8; 514/24; 514/42; 514/54
[58] Field of Search .................................. 424/1.69, 1.73, 424/85.1, 85.2, 85.4, 178.1, 179.1, 181.1; 514/2.8, 12.21, 24, 42, 44, 54

[56] References Cited

U.S. PATENT DOCUMENTS

| | | | |
|---|---|---|---|
| 4,410,688 | 10/1983 | Denkewalter et al. | 528/328 |
| 4,507,466 | 3/1985 | Tomalia et al. | 528/332 |
| 4,558,120 | 12/1985 | Tomalia et al. | 528/363 |
| 4,568,737 | 2/1986 | Tomalia et al. | 528/332 |
| 4,587,329 | 5/1986 | Tomalia et al. | 528/363 |
| 4,885,153 | 12/1989 | Wilbur et al. | 530/402 |
| 4,897,255 | 1/1990 | Fritzberg et al. | 530/391.5 |
| 4,965,392 | 10/1990 | Fritzberg et al. | 558/254 |
| 5,057,302 | 10/1991 | Johnson et al. | 530/345 |
| 5,310,536 | 5/1994 | Srinivasan | 424/1.65 |
| 5,554,386 | 9/1996 | Groman et al. | 424/488 |
| 5,624,896 | 4/1997 | Axworthy et al. | 514/8 |
| 5,635,383 | 6/1997 | Wu et al. | 435/172.3 |

FOREIGN PATENT DOCUMENTS

| | | |
|---|---|---|
| WO 89/10140 | 11/1989 | WIPO . |
| WO 91/09628 | 12/1989 | WIPO . |
| WO 94/19024 | 9/1994 | WIPO . |

OTHER PUBLICATIONS

Biessen et al., "Synthesis of Cluster Galactosides with High Affinity for the Hepatic Asialoglocoprotein Receptor," *J. Med. Chem.* 38: 1538–1546, 1995.

Findeis, "Stepwise Synthesis of a GaINAc–containing Cluster Glycoside Ligand of the Asiaglycoprotein Receptor," *Int. J. Peptide Protein Res.* 43: 477–485, 1994.

Galli et al., "A Radiopharmaceutical for the Study of the Liver: $^{99m}$Tc–DTPA–Asialo–Orosomucoid I: Radiochemical and Animal Distribution Studies," *J. Nucl. Med.* 32(2): 110–116, 1988.

Hank et al., "Gene Transfer into Hepatocytes Using Asialoglycoprotein Receptor Mediated Endocytosis of DNA Complexed with an Artificial Tetra–Antennary Galactose Ligand," *Bioconjugate Chemistry* 3(6): 533–539, 1992.

Jansen et al., "Hepatic Endocytosis of Various Types of Mannose–terminated Albumins," *J. of Biological Chem.* 266(5): 3343–3348, 1991.

Mauk et al., "Targeting of Lipid Vesicles: Specificity of Carbohydrate Receptor Analogues for Leukocytes in Mice," *Proc. Natl. Acad. Sci. USA* 77(8): 4430–4, 1980.

(List continued on next page.)

*Primary Examiner*—Jeffrey E. Russel
*Attorney, Agent, or Firm*—Seed and Berry LLP

[57] ABSTRACT

Hepatic-directed compounds, reagents useful in making such compounds and associated methods and compositions are disclosed. Hepatic-directed compounds are processed by metabolic mechanisms, which generally differ in degree or in kind from the metabolic mechanisms encountered by compounds which are not so directed. Hepatic-directed compounds useful in the methods disclosed include a hexose cluster characterized by multiple hexose residues connected in an iteratively branched configuration. In one embodiment, the hexose cluster comprises at least four hexose residues with each branch of the configuration having two prongs. In another embodiment, the hexose cluster comprises at least nine hexose residues with each branch of the configuration having three prongs.

5 Claims, 7 Drawing Sheets

OTHER PUBLICATIONS

McKee et al., "Preparation of Asialoorosomucoid–Polylysine Conjugates," *Bioconjuate Chem.* 5: 306–311, 1994.

Merwin et al., "Targeted Delivery of DNA Using YEE (GaINAcAH)$_3$, a Synthetic Glycopeptide Ligand for the Asialoglycoprotein Receptor," *Bioconjugate Chem.* 5: 612–620, 1994.

Morell et al., "The Role of Sialic Acid in Determining the Survival of Glycoproteins in the Circulation," *J. Biol. Chem.* 246(1): 1461–1467, 1971.

Ponpipom et al., "Cell surface carbohydrates for targeting studies," *Can. J. Chem.* 58: 214, 1980.

Sharma et al., "Inactivation and Clearance of an anti–CEA carboxypeptidase G2 Conjugated in Blood after Localization in a Xenograft Model," *Br. J. Cancer 61*: 659–662, 1990.

Sharon et al., "Carbohydrates in Cell Recognition," *Scientific American* 268(1): 82–89, 1993.

Tolleshaug, "Binding and Internalization of Asialo–glycoproteins by Isolated Rat Hepatocytes," *Int. J. Biochem.* 13: 45–51, 1981.

Vera et al., "Tc–99m Galactosyl–Neoglycoalbumin: In Vitro Characterization of Receptor–Mediated Binding," *J. Nucl. Med.* 25(7): 779–787, 1984.

Wall et al., "The Galactose–Specific Recognition System of Mammalian Liver: the Route of Ligand Internalization in Rat Hepatocytes," *Cell 21*: 79–93, 1980.

Weber et al., "Enhanced Kidney Clearance with an Ester–Linked $^{99m}$Tc–Radiolabeled Antibody Fab'–Chelator Conjugate," *Bioconjugate Chem. 1*: 431–437, 1990.

Weigel, *GlyConjugates Composition, Structure and Function*, Chapter 14, "Mechanisms and Control of Glyconjugate Turnover," edited by Allen et al., Marcel Dekker, Inc., New York, 421–97, 1992.

Weigel, *Subcellular Biochemistry, vol. 19, Endocytic Components: Identification and Characterization*, Bergeron et al. (eds.), Plenum Press, New York, 1993, Chapter 5, "Endocytosis and Function of the Hepatic Asialoglycoprotein Receptor," pp. 125–161.

Haensler et al. Synthesis and Characterization of a Trigalactosylated . . . Bioconjugate Chem. vol. 4, No. 1, pp. 85–93, 1993.

Krantz et al. Attachment of Thioglycosides to Proteins Enhancement . . . Biochemistry. vol. 15, No. 18, pp. 3963–3968, 1976.

Lee et al. Preparation of Cluster Glycosides . . . Glycoconjugate. vol. 4, pp. 317–328, 1987.

Lee et al. 2–Imino–2–Methoxyethyl 1–Thioglycosides . . . Biochemistry. vol. 15, No. 18, pp. 3956–3963, 1976.

Makhlouf et al. Antisera Specificities to β–D–Galactopyranoside . . . Carbohydrate Research. vol. 132, pp. 93–103, 1984.

Plank et al. Gene Transfer into Hepatocytes Using . . . Bioconjugate Chem. vol. 3, No. 6, pp. 533–539, 1992.

Van der Sluijs et al. Drug Targeting to the Liver . . . Hepatology, vol. 6, No. 4, pp. 723–728, 1986.

N, N' - Bis (2-disulfidyl-4-methylphenyl) - γ,γ' - diamino isovalerate N-hydroxysuccinimide

METHODS OF USING HEPATIC-DIRECTED COMPOUNDS IN PRETARGETING STRATEGIES

This application is a divisional of U.S. application Ser. No. 08/351,651, filed Dec. 7, 1994.

TECHNICAL FIELD

The present invention relates to hepatic-directed compounds, reagents useful in making such compounds and associated methods and compositions. Hepatic-directed compounds are processed by metabolic mechanisms, which generally differ in degree or in kind from the metabolic mechanisms encountered by compounds which are not so directed. Hepatic-directed compounds are eliminated from the recipient via the liver and, generally, exhibit a decreased serum half-life in comparison to non-directed counterpart compounds.

BACKGROUND OF THE INVENTION

Conventional cancer therapy is plagued by the problem that the generally attainable targeting ratio (ratio of administered dose localizing to tumor versus administered dose circulating in blood or ratio of administered dose localizing to tumor versus administered dose migrating to bone marrow) is low. Improvement in targeting ratio dose to tumor is sought.

One method employed in efforts to improve targeting ratio is to decrease the serum concentration of a compound. One method of decreasing the serum concentration of an administered compound is to subsequently administer a molecule designed to be eliminated rapidly via the liver and to bind to the first administered compound. Galactose-HSA-biotin conjugates, discussed in PCT patent application No. PCT/US93/05406 facilitate elimination of circulating targeting agent-streptavidin conjugates from the bloodstream. Galactosylated antibodies directed to a portion of a previously administered molecule have also been employed for this purpose.

In addition, the liver is susceptible to a variety of conditions for which liver delivery of an active agent would be useful. In these circumstances, delivery of active agent via the hepatic artery has been proposed. This methodology is invasive and, therefore, other methods of active agent delivery to the liver are sought.

SUMMARY OF THE INVENTION

The present invention is directed to hepatic-directed compounds, reagents and methods for the preparation and use of such compounds. Hepatic-directed compounds may be employed to deliver an active agent to the liver, to improve targeting ratio, or both. Hepatic directed compounds may also be employed to direct previously administered moieties or toxic or potentially toxic moieties to a liver metabolic pathway for elimination.

One embodiment of hepatic-directed compounds of the present invention generally includes a director moiety and an active agent. In this embodiment of the present invention, one or more active agents may be directly or indirectly bound to the director moiety. Examples of indirect binding include the use of polymeric carriers, liposomes, particulate dosage forms and the like. Such hepatic-directed compounds are especially useful for delivery of active agents to the liver to address liver conditions. The director moiety directs localization of the hepatic-directed compound to the liver, and the active agent addresses the ailment.

In the situation wherein an improvement in targeting ratio is sought, hepatic-directed compounds of the present invention generally include a targeting moiety directed to the target cell population to be treated/diagnosed as well as a director and, optionally, an active agent-type effector. Under these circumstances, the targeting moiety directs the localization of the compound to target cells, the active agent addresses the ailment, and the director moiety facilitates removal of the compound from circulation via the liver thereby reducing exposure of the recipient's normal tissues to the active agent.

In another embodiment of the present invention, the hepatic-directed compounds of the present invention generally include a director moiety and a binding moiety, which recognizes a previously administered agent or other toxic agent in the bloodstream or extravascular fluid space of the recipient. Such hepatic-directed compounds are especially useful for clearance of previously administered molecules, such as targeting moiety-receptor constructs designed to accrete to target sites and facilitate localization of subsequently administered active agent-containing molecules that recognize the receptors. Consequently, this embodiment of the present invention is particularly amenable to use in pretargeting protocols as described herein.

Alternatively, the binding moiety may be directed to toxic or potentially toxic moieties located in the recipient's circulation or extravascular fluid space. The director moiety directs localization of the hepatic-directed compound to the liver, and the binding moiety binds to the molecule to be eliminated via the hepatic pathway.

Preferred director moieties of the present invention are branched sugar constructs (i.e, sugar clusters) that are recognized by a population of receptors on the liver. Exemplary sugars for this purpose are galactose and mannose. The branched configuration typically facilitates recognition of the sugars by liver receptors, as such receptors often most efficiently process clusters of sugars of certain configurations.

More preferred director moieties according to the present invention contain galactose or galactose derivatives. An embodiment of such preferred director moieties incorporates a multiple of 4 galactoses. Director moieties having 4, 8, 16 and 32 galactose residues are generally preferred for use in pretargeting aspects of the present invention. Alternative branching structures, such as those having 3, 9, 27, etc. sugars are also contemplated by the present invention.

Director moieties may be incorporated into hepatic-directed compounds using appropriate reagents therefor. Director reagents of the present invention incorporate a galactose cluster, such as those described above, and a functional group, such as an amine active ester, maleimide, alkyl halide, hydrazide, thiol, imidate, aldehyde or the like.

DETAILED DESCRIPTION OF THE INVENTION

Figure 1:
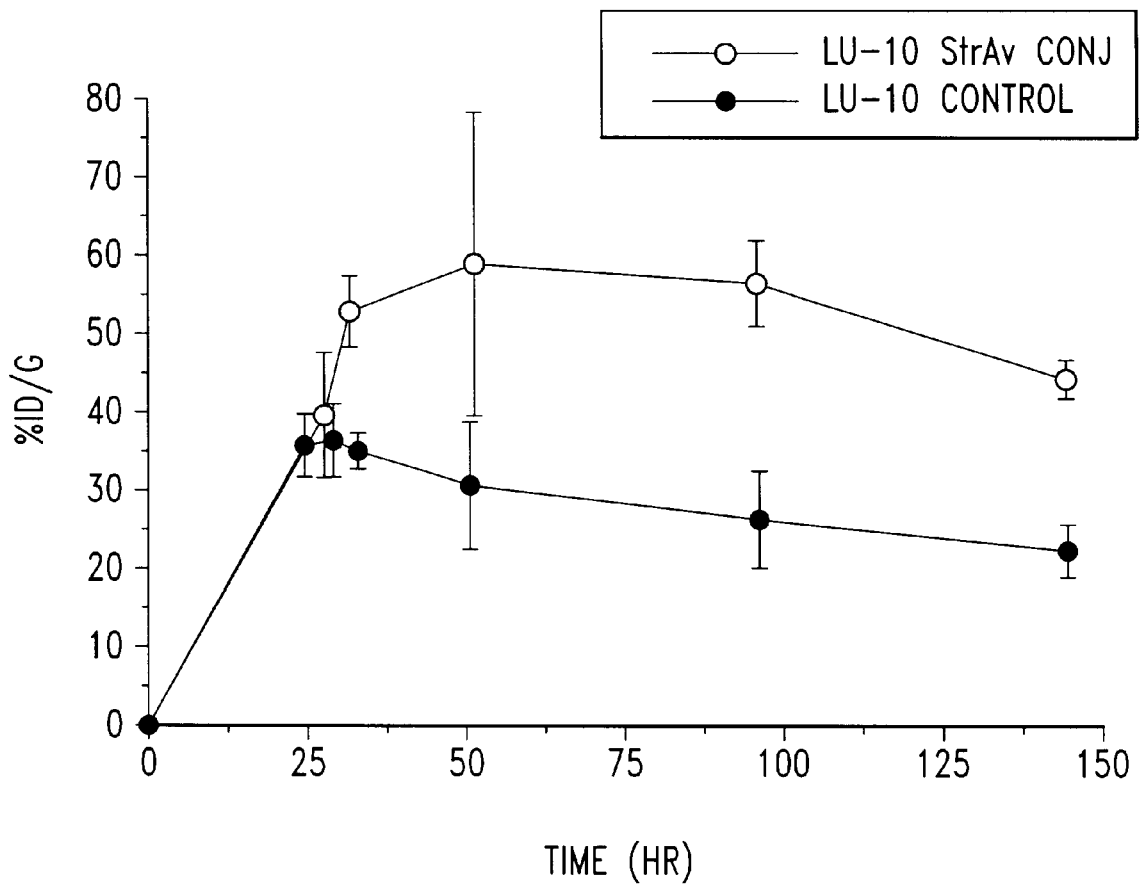
FIG. 1 illustrates the tumor uptake profile of NR-LU-10-streptavidin conjugate (LU-10-StrAv) in comparison to a control profile of native NR-LU-10 whole antibody.

Prior to setting forth the invention, it may be helpful to set forth definitions of certain terms to be used within the disclosure.

Targeting moiety: A molecule that binds to a defined population of cells. The targeting moiety may bind a receptor, an oligonucleotide, an enzymatic substrate, an antigenic determinant, or other binding site present on or in the target cell population. Antibody is used throughout the specification as a prototypical example of a targeting moiety. Tumor is used as a prototypical example of a target in describing the present invention.

Licand/anti-licand pair: A complementary/anti-complementary set of molecules that demonstrate specific binding, generally of relatively high affinity. Exemplary ligand/anti-ligand pairs include zinc finger protein/dsDNA fragment, enzyme/inhibitor, hapten/antibody, lectin/carbohydrate, ligand/receptor, S-protein/S-peptide, head activator protein (which binds to itself), cystatin-C/cathepsin B, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivatized to exhibit structural features that direct the uptake thereof, e.g., galactose residues that direct liver uptake. Avidin and streptavidin are used herein as prototypical anti-ligands.

Avidin: As defined herein, "avidin" includes avidin, streptavidin and derivatives and analogs thereof that are capable of high affinity, multivalent or univalent binding of biotin.

Ligand: As defined herein, a "ligand" is a relatively small, soluble molecule that binds with high affinity by anti-ligand and preferably exhibits rapid serum, blood and/or whole body clearance when administered intravenously in an animal or human. Biotin is used as the prototypical ligand.

Lower Affinity Ligand or Lower Affinity Anti-Liqand: A ligand or anti-ligand that binds to its complementary ligand-anti-ligand pair member with an affinity that is less than the affinity with which native ligand or anti-ligand binds the complementary member. Preferably, lower affinity ligands and anti-ligands exhibit between from about $10^{-6}$ to $10^{-10}$M binding affinity for the native form of the complementary anti-ligand or ligand. For avidin/streptavidin and other extremely high affinity binding molecules, however, lower affinity may range between $10^{-6}$ to $10^{-13}$M. Lower affinity ligands and anti-ligands may be employed in clearing agents or in active agent-containing conjugates of the present invention.

Active Agent: A diagnostic or therapeutic agent ("the payload"), including radionuclides, drugs, anti-tumor agents, toxins and the like. Radionuclide therapeutic agents are used as prototypical active agents.

$N_xS_y$ Chelates: As defined herein, the term "$N_xS_y$ chelates" includes bifunctional chelators that are capable of (i) coordinately binding a metal or radiometal and (ii) covalently attaching to a targeting moiety, ligand or anti-ligand. Particularly preferred $N_xS_y$ chelates have $N_2S_2$ and $N_3S$ cores. Exemplary $N_xS_y$ chelates are described in Fritzberg et al., *Proc. Natl. Acad. Sci. USA* 85:4024–29, 1988; in Weber et al., *Bioconi. Chem.* 1:431–37, 1990; and in the references cited therein, for instance.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

Clearing Agent: An agent capable of binding, complexing or otherwise associating with an administered moiety (e.g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

Conjugate: A conjugate encompasses chemical conjugates (covalently or non-covalently bound), fusion proteins and the like.

Hepatic-directedected compounds: Conjugates generally including a director and an effector. One or more effector molecules may be directly or indirectly bound to one or more directors.

Indirect Binding: Binding of effector molecule(s) to director molecule(s) via a carrier, such as a polymer, a liposome, a particulate dosage form or the like.

Direct Binding: Direct chemical linkage between components of a hepatic-directed compound or such chemical linkages incorporating a spacer, extender, or other chemical linker molecule designed as a linker rather than as a carrier.

Director: A moiety capable of directing the clearance of a component to which it is bound upon administration or of a component to which it becomes bound in vivo. Director moieties of the present invention direct clearance via the hepatic pathway.

Effector: A moiety capable of achieving a desired effect for a specific application, such as an active agent; a binding moiety including a ligand, an anti-ligand or the like; a targeting moiety; or the like.

Binding Moiety: A ligand, anti-ligand or other moiety capable of in vivo association with a previously administered molecule (bearing the complementary ligand or anti-ligand, for example) or with another toxic or potentially toxic molecule present in the recipient's circulation or extravascular fluid space via recognition by the binding moiety of an epitope associated with the toxic or potentially toxic molecule.

Sucar cluster: A director moiety having a plurality of sugar residues configured to be recognized by a liver receptor. Such clusters are preferably constructed of sugar residues connected in a branched configuration, and are attached to other components of a sugar cluster-containing conjugate via a single point of attachment. Preferably, the branching network consists of two or three pronged branches, i.e., consists of 2, 4, 8, 16, 32 or 64 sugar residues or consists of 3, 9, 27, or 81 sugar residues.

Sugar Cluster Clearing Acent: A hepatic directed compound designed for use as a clearing agent in a pretargeting protocol incorporating a sugar cluster director.

Galactose cluster: A director moiety having from about 3 to about 100 galactose residues connected in a branched configuration, with constructs involving less than 50 galactose residues preferred. Preferably, the branching network consists of two or three pronged branches, i.e., consists of 2, 4, 8, 16, 32 or 64 galactose residues or consists of 3, 9, 27, or 81 galactose residues.

Galactose Cluster Clearing Agent: A hepatic directed compound designed for use as a clearing agent in a pretargeting protocol incorporating a galactose cluster director.

Director Reagent: A reagent comprising a directing portion and one or more functional groups for binding to an effecting portion to form a hepatic-directed compound.

An embodiment of the present invention is directed to hepatic-directed compounds suitable for delivery of active agent effectors to liver targets, which hepatic-directed compounds include:

a director including a cluster of sugar residues which is capable of directing liver uptake of the compound; and an active agent directly or indirectly bound to the director capable of diagnostic or therapeutic application with respect to a liver ailment.

In this embodiment of the present invention, the director serves to deliver the active agent to the liver target. The active agent provides a diagnostic or therapeutic benefit at the liver target. Further, an optional active agent carrier facilitates delivery of a plurality of active agent molecules or multiple active agents to the liver target.

Another embodiment of the present invention is directed to hepatic-directed compounds suitable for reduction of background active agent or targeting moiety concentration in the circulation or extravascular fluid space of a recipient, which hepatic-directed compounds include:

a director including a cluster of sugar residues which is capable of directing liver uptake of the compound;

a targeting moiety which localizes to a target of interest, which targeting moiety optionally is covalently or non-covalently bound to a receptor; and, optionally, an active agent, directly or indirectly bound to the director or to the targeting moiety (preferably to the targeting moiety), capable of diagnostic or therapeutic application with respect to the target.

In this embodiment of the present invention, the targeting moiety localizes to target, either delivering a receptor or an active agent thereto. The director promotes elimination of the hepatic-directed moiety via the liver to reduce non-target accumulation of the hepatic-directed molecule. The optional receptor, if employed, provides a binding site for a subsequently administered active agent-containing construct. The optional active agent, if employed, provides a diagnostic or therapeutic benefit at the target. Further, an optional active agent carrier facilitates delivery of a plurality of active agent molecules or multiple active agents to the target.

Further embodiments of the present invention are directed to hepatic-directed compounds suitable for directing the metabolic pathway for elimination of molecules present in the circulation or extravascular fluid space of a recipient, which hepatic-directed compounds include:

a director including a cluster of sugar residues which is capable of directing liver uptake the compound; and a binding moiety directly or indirectly bound to the director capable of in vivo complexation with certain molecules present in the circulation or extravascular fluid space of the recipient.

In this embodiment of the present invention, the director serves to direct the biodistribution of the hepatic-directed molecule and the constructs with which it becomes associated in vivo. The binding moiety facilitates in vivo association with previously administered compounds or with toxic or potentially toxic moieties resident in the circulation or extravascular fluid space of the recipient. Further, an optional binding agent carrier facilitates transport of a plurality of binding agent molecules in the circulation or extravascular fluid space.

When radionuclides are employed as active agents, constructs of the present invention include: hepatic directed compounds incorporating chelates for subsequent complexation of radionuclide therein (conjugation via the post-formed approach) as well as hepatic-directed compounds incorporating radionuclides previously complexed with radionuclide (conjugation via the pre-formed approach).

Hexose clusters are preferably employed as directors in the practice of the present invention. Galactose clusters are the prototypical hexose clusters employed for the purposes of this description. Design of hexose clusters of the present invention is conducted with the following criteria in mind, as set forth in the context of the design of a galactose cluster:

1) Number of Galactoses in a Cluster;
2) Distance Between Galactoses in the Cluster; and
3) Distance Between Galactose Cluster and a Conjugate Component Which Must Bind to Circulating Molecules or to Target.

With regard to criterion number 1, literature indicates that galactose receptors on the surface of human hepatocytes are grouped as heterotrimers and, perhaps, bis-heterotrimers. See, for example, Hardy et al., *Biochemistry*, 24: 22–8, 1985. For optimal affinity to such receptors, the present inventors believe that each galactose cluster should preferably contain at least three galactose residues. In general, the greater the number of sugars in a cluster, the greater the propensity for the cluster to be recognized by liver receptors.

Increased sugar cluster size may impair binding to circulating molecules or to target. If significant impairment in such binding (e.g. reduction to <20% of native targeting moiety or binding moiety binding capability) is observed, a longer linker should be employed between the two moieties or such large clusters should not be used in hepatic-directed compounds of the present invention. The present invention embraces hexose clusters with any number of hexose residues or any mixture thereof which results in efficacious liver clearance of the resultant hepatic-directed molecule.

With respect to criterion number 2, the galactose receptors within each trimer are separated from each other by distances of 15, 22 and 25 angstroms. Consequently, the present inventors believe that the galactoses within a cluster should preferably be separated by flexible linkers allowing separation of at least 25 angstroms. The spacing between sugar residues is likely to be more important if the number of sugar residues is small. With larger constructs, appropriate spacing is likely to occur with respect to sugar residues that are not immediate neighbors (i.e., sugar residues that are farther apart than those that are immediate neighbor). Assuming an average bond length of 1.5 angstroms, preferred sugar clusters of the present invention are characterized by separation of neighboring sugar residues by about 10 bond lengths or more. Other preferred constructs involve galactose clusters characterized by separation of neighboring sugar residues by about 25 bond lengths or more.

Regarding criterion number 3, the distance between the targeting moiety and/or the binding moiety component and the galactose cluster should be sufficient to obviate any adverse steric effects upon binding capability of those components caused by the size or orientation of the galactose cluster. This distance is preferably greater than about 7 bond lengths or about 10 angstroms. If necessary, an extender molecule is incorporated between the relevant conjugate components to provide the requisite distance. For example, such extenders may be positioned between the galactose cluster and a linker (which joins the galactose cluster and the targeting or bindinding component) or between the targeting or binding component and the linker to provide the requisite distance.

While the foregoing parameters appear to be optimal for galactose, it should be noted that these factors may vary with other hexoses or mixtures thereof, which may or may not bind to the same receptors, or may bind differently. Given the teachings in this application, one skilled in the art can, using available synthesis techniques, prepare constructs incorporating other hexose clusters and identify those constructs which provide optimal performance.

Any branched sugar structures that meet the criteria described above may be employed in the practice of the present invention. Preferred galactose clusters of the present invention are of the following structures:

wherein X is preferably H or methyl, resulting in galactose clusters bearing 4, 8, 16 and 32 galactose residues, respectively. Further iteration in the branching scheme allows expansion of the galactose cluster to include 32, 64, etc. galactose residues. In addition, the linker moiety between the sugar itself and the branching structure (shown as —S—(CH$_2$)$_4$—NX—) may be variable in length.

Alternative branching structures may also be employed in the design of galactose clusters in accordance with the present invention. For example, other constructs wherein the branching results in a doubling of the number of galactose residues may be employed. In addition, constructs wherein branching results in a tripling or other convenient multiplying of the number of galactose residues are also contemplated by the present invention.

Another potential branching construction is based upon the molecule bis-homotris: (HO—CH$_2$)$_3$—C—NH$_2$. The sulfhydryl-containing derivative of this molecule may also be used. In this embodiment of the present invention, each arm of the bis-homotris molecule is extended and terminated in a carboxylic acid: (HO$_2$C—(CH$_2$)$_y$—Z—(CH$_2$)$_3$—C—NH$_2$, where Z is S or O and y ranges from 1 to about 10. For this embodiment of the present invention, a preferred galactose cluster is characterized by the following structures:

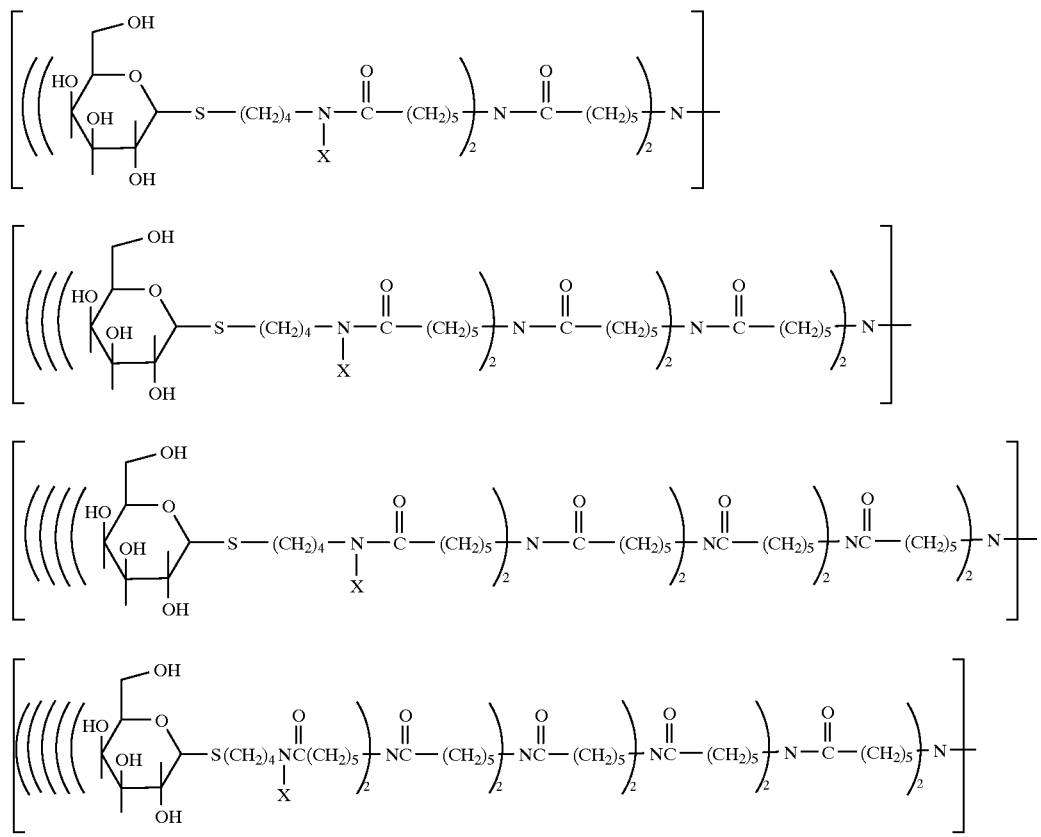

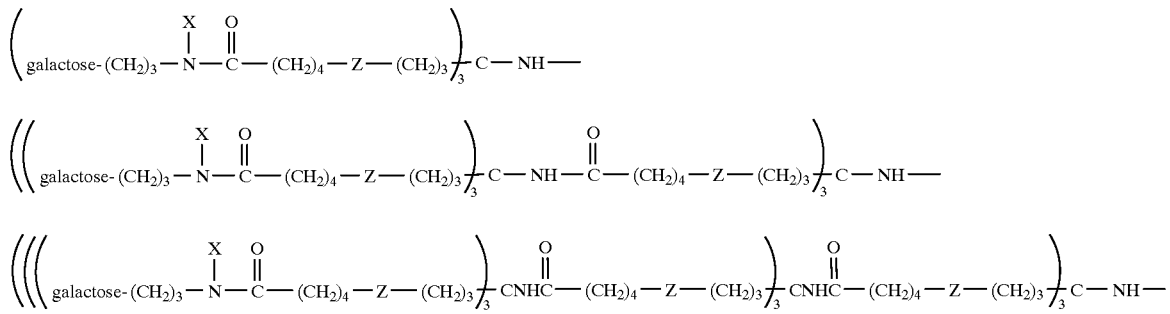

wherein X is preferably H or methyl; y ranges from 1 to about 10; and Z is O or S. The above structures bear 3, 9 and 27 galactose residues, respectively. Further iteration of the branching allows expansion to include 81, etc. galactose residues.

Also, X may be a lower alkyl moiety different from methyl, such as ethyl, t-butyl and the like. X may also be a lower alkyl group bearing a heteroatom, such as a lower alkyl acid, ester, aldehyde, ketone or ether. The purpose of X is to provide steric inhibition to metabolic/catabolic enzymes that may cleave the amide bond. X should not alter the function of the agent to which it is attached and, therefore, may be altered to increase/decrease solubility, charge or other physical property as necessary for a given application.

Galactose cluster director molecules are incorporated into hepatic-directed compounds using director reagents. A family of director reagents having different functional groups can be employed for binding of such director reagents to various other molecules to form a variety of hepatic-directed compounds in accordance with the present invention. A preferred family of director reagents of the present invention may be represented by the following formula:

thiols, hydroxyls, amines and the like. Hydrazide groups facilitate conjugation to activated esters, aldehydes, ketones and the like. Thiols may be employed to conjugate the galactose cluster to thiols, maleimides, alkyl halides, alpha-halo-ketones, and the like. Imidates facilitate conjugation to amines the like. Aldehydes may be employed for conjugation to amines, via Schiff base formation with or without reduction, and the like.

These same X' functional groups can be employed in director reagents for any director reagent family of the present invention. A family of director reagents is formed from a single molecule structured as follows: Hexose cluster-base (in the structural sense) functionality-available (in the steric sense) functionality, wherein the base functionality is amenable to derivatization to provide X' moieties bearing available functional groups that are the same or different from the base functionality. Examples of base functionalities are —NH$_2$, active ester, maleimide, sulfhydryl, and the like. For an —NH$_2$ base functionality, appropriate X' groups include the following:

amine;
—NR—CO—(CH$_2$)$_2$—O—NHS;
—NR—CO—(CH$_2$)$_2$—O—NHS—SO$_3$Na;

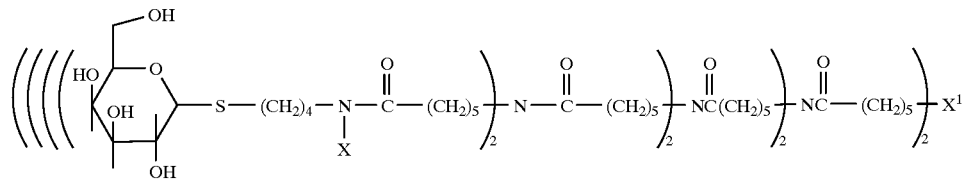

wherein X' bears an available functional group and X is H or methyl, resulting in galactose clusters bearing 16 galactose residues. Other related director reagents bearing an alternative multiple of 4 galactose residues are analogously structured. The available functional group of X' is selected in accordance with the nature of the other component(s) of the hepatic-directed compound. Examples of useful X' functional groups include amines, activated esters, maleimides, isocyanates, isothiocyanates alkyl halide (e.g., iodoacetate), alpha-halo-ketones, alpha-halo-acids, hydrazides, thiols, imidates, aldehydes, photolytic conjugating groups, and the like.

For example, activated esters may be employed to conjugate the galactose cluster to amines (primary or secondary), hydroxyls, sulfhydryls, and the like. Maleimides facilitate conjugation to thiols and the like. Isocyanates and isothiocyanates may be employed for conjugation to amines and the like. Alkyl halides are useful for conjugation to —NR—CO—(CH$_2$)$_2$—O—tetrafluorophenyl;
—maleimide;
—NR-extender-maleimide, wherein the extender is an aminocaproate group, —(CH$_2$)$_n$ or the like, wherein n ranges from 1 to about 10;
—3(2-pyridyldithio)propionamide;
—NR—CO—CH$_2$—SH;
—NR—CO—CH$_2$—halide, preferably I or Br;
—NR—CO—NH—NH$_2$;
—NR—CO—(CH$_2$)$_n$—CO—NH—NH$_2$, wherein n ranges from 1 to about 10;
—NR—CO—(CH$_2$)$_2$C=NH$_2$+—OCH$_3$;
—NR—CO—CH$_2$—p—N$_3$—phenyl;
and the like.

In addition, the amine base functionality may additionally be N-alkylated to enhance stability against metabolic degradation or retention within hepatocytes. Consequently, R may be H, CH$_3$, CH$_2$COOH or the like.

Example VII indicates a method for preparation of a related member of the above-identified director reagent family (wherein X' is an amine and the galactose cluster incorporates 8 galactose residues). In addition, preparation of an embodiment of hepatic-directed compounds from such galactose cluster director reagents is described in Examples VIII and IX.

Hepatic-directedected molecules of the present invention may be formed using suitable linkers. Two component hepatic-directed molecules are formed using a bifunctional linker. For three component hepatic-directed compounds wherein none of the components are characterized by greater than one functional group suitable and available for conjugation to other components, trifunctional linkers are preferred. For three component hepatic-directed molecules wherein at least one of the components has two or more functional groups available and suitable for conjugation with other components, two bifunctional linkers are preferred for conjugate formation. Any linker or linker combination useful for linking the hepatic-directed compound component may be employed. Suitable trifunctional and bifunctional linkers are set forth below.

Functional groups that are "available" for conjugation are those that are not prevented by steric constraints from conjugate formation. Functional groups that are "nsuitable" for conjugation are those that are capable, in a chemical sense, of reacting with available functional groups associated with other conjugate components. In addition, conjugation of "suitable" functional groups does not substantially impair a necessary function of the component with which the functional group is associated. For example, a functional group located in the complementarity determining region of an antibody targeting moiety will generally not be "suitable" for conjugation, because the targeting ability of the antibody is likely to be substantially impaired by such binding.

Targeting moiety, binding moiety or active agent, and galactose cluster components of a three component hepatic-directed compound can be joined via a trifunctional linker, provided one of such components has the characteristics discussed above. Suitable trifunctional linkers are amenable to binding with functional groups available on the three conjugate components or any extender moieties employed in conjugate construction. A useful trifunctional linker is lysine, wherein the alpha-amino, epsilon-amino and carboxyl functional groups are used. One skilled in the art is capable of identifying other trifunctional linkers as well as of using such linkers as set forth herein.

Extender molecules useful in the present invention are bifunctional moieties capable of binding with either a targeting component, for example, and the linker or the galactose cluster component and the linker. Suitable extender molecules include aminocaproate moieties, HS—(CH$_2$)$_n$COOH or an activated ester form thereof wherein n ranges from 2 to about 5, 4-aminobutanethiol, and the like. One of ordinary skill in the art is capable of identifying and using other suitable extender molecules as described herein. Alternatively, the extender function can be served by an appropriately constructed linker.

Also, binding facilitation moieties may also be employed in the present invention. Such moieties are bifunctional and facilitate binding the conjugate components, e.g., galactose cluster, targeting moiety, binding moiety, active agent, chelate, linker, and extender. Examples of such binding facilitation moieties include urea functionalities, thiourea functionalities, succinate bridges, maleimides and the like. Such binding facilitation moieties are amenable to identification and use by those skilled in the art.

An example of a linker-extender-binder facilitation system is shown below:

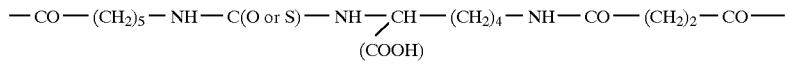

wherein the alpha-amine of the lysine linker is bound via a urea or thiourea functionality to an amino caproate spacer (which, in turn, binds to a galactose cluster that is not shown); the lysine carboxylate is available for linkage to a chelate (not shown); and the epsilon-amine of the lysine linker-is available for linkage to a lysine residue of the targeting component, for example, (not shown) via a succinate bridge. Other amino acid residues of the targeting component component, such as cysteine, may also be employed for binding purposes. Alternatively a maleimide—S—(CH$_2$)$_n$CO—binding facilitation moiety-extender combination may be employed to link the sugar residue with the lysine.

Alternatively, the galactose cluster may be linked to the chelate component which, in turn, is linked to the targeting component of the conjugate, for example, via two or more bifunctional linkers. Preferably, the targeting component, for example of the conjugate is attached last in the formation of a galactose cluster-containing conjugate. Suitable bifunctional linkers, such as bis-N,N-(6-(1-hydroxycarbonylhexyl) amine and the like, and linking methodologies can be identified and employed by one skilled in the art.

Preferably, the hepatic-directed compounds of the present invention designed for targeting to locations in the extravascular fluid space or for clearing molecules present in the extravascular fluid space are of a low enough molecular weight to provide for efficient diffusion into the extravascular fluid space. Molecular weights for such entities will preferably range from about 1500 to about 20,000 daltons.

When.employing a radionuclide active agent, preparation of the hepatic-directed compound components via chemical methods can occur either prior to (post-formed approach) or following (pre-formed approach) complexation of the radionuclide within the chelate. Such conjugation is preferably conducted following radiometal complexation, however, unless the chelate employed in the conjugate is capable of binding the radionuclide rapidly at room temperature.

The "targeting moiety" of the present invention binds to a defined target cell population, such as tumor cells. Preferred targeting moieties useful in this regard include antibody and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, *Univ. Mich. Med. Bull.*, 20: 284–6, 1956), affinity-purified polyclonal or fragments thereof (Chao et al., *Res. Comm. in Chem. Path. & Pharm.*, 9: 749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, *Nature*, 256: 495–97, 1975; *Eur. J. Immunol.*, 6: 511–19, 1976.

Human monoclonal antibodies or "humanized" murine antibody are also useful as targeting moieties in accordance with the present invention. For example, murine-monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.q, in a manner similar to that disclosed in European Patent Application No. 0,411,893 A2. Some murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Types of active agents (diagnostic or therapeutic) useful herein include toxins, anti-tumor agents, drugs and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

Preferred toxins in this regard include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein. Extremely highly toxic toxins, such as palytoxin and the like, are also contemplated for use in the practice of the present invention.

Preferred drugs suitable for use herein include conventional chemotherapeutics, such as vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. A particularly preferred drug within the present invention is a trichothecene.

Trichothecenes are drugs produced by soil fungi of the class *Fungi imperfecti* or isolated from *Baccharus megapotamica* (Bamburg, J. R. *Proc. Molec. Subcell. Biol.* 8:41–110, 1983; Jarvis & Mazzola, *Acc. Chem. Res.* 15:338–395, 1982). They appear to be the most toxic molecules that contain only carbon, hydrogen and oxygen (Tamm, C. *Fortschr. Chem. Ora. Naturst.* 31:61–117, 1974). They are all reported to act at the level of the ribosome as inhibitors of protein synthesis at the initiation, elongation, or termination phases.

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4;744,981 and 4,906,452 (incorporated herein by reference). Representative examples of Group A simple trichothecenes include: Scirpene, Roridin C, dihydrotrichothecene, Scirpen-4, 8-diol, Verrucarol, Scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,15-diacetoxyscirpenol, 7-hydroxydiacetoxyscirpenol, 8-hydroxydiacetoxy-scirpenol (Neosolaniol), 7,8-dihydroxydiacetoxyscirpenol, 7-hydroxy-8-acetyldiacetoxyscirpenol, 8-acetylneosolaniol, NT-1, NT-2, HT-2, T-2, and acetyl T-2 toxin.

Representative examples of Group B simple trichothecenes include: Trichothecolone, Trichothecin, deoxynivalenol, 3-acetyldeoxynivalenol, 5-acetyldeoxynivalenol, 3,15-diacetyldeoxynivalenol, Nivalenol, 4-acetylnivalenol (Fusarenon-X), 4,15-idacetylnivalenol, 4,7,15-triacetylnivalenol, and tetra-acetylnivalenol. Representative examples of Group C simple trichothecenes include: Crotocol and Crotocin. Representative macrocyclic trichothecenes include Verrucarin A, Verrucarin B, Verrucarin J (Satratoxin C), Roridin A, Roridin D, Roridin E (Satratoxin D), Roridin H, Satratoxin F, Satratoxin G, Satratoxin H, Vertisporin, Mytoxin A, Mytoxin C, Mytoxin B, Myrotoxin A, Myrotoxin B, Myrotoxin C, Myrotoxin D, Roritoxin A, Roritoxin B, and Roritoxin D. In addition, the general "trichothecene" sesquiterpenoid ring structure is also present in compounds termed "baccharins" isolated from the higher plant *Baccharis megapotamica*, and these are described in the literature, for instance as disclosed by Jarvis et al. (chemistry of Alleopathy, ACS Symposium Series No. 268: ed. A. C. Thompson, 1984, pp. 149–159).

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl) -3-(2, 6-dioxo-3-piperidyl) -1-nitrosourea, N,N'-hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxy-doxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycyidine (see *NCI Investiqational Drugs, Pharmaceutical Data* 1987, NIH Publication No. 88–2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use. Radionucliydes are well-known in the art and include $^{123}I$, $^{125}I$, $^{130}I$, $^{131}I$, $^{133}I$, $^{135}I$, $^{47}Sc$, $^{72}As$, $^{72}Se$, $^{90}y$, $^{88}y$, $^{97}Ru$, $^{100}Pd$, $^{101m}Rh$, $^{119}Sb$, $^{128}Ba$, $^{197}Hg$, $^{211}At$, $^{212}Bi$, $^{153}Sm$, $^{169}Eu$, $^{212}Pb$, $^{109}Pd$, $^{111}In$, $^{67}Ga$, $^{68}Ga$, $^{64}Cu$, $^{67}Cu$, $^{75}Br$, $^{76}Br$, $^{77}Br$, $^{99m}Tc$, $^{11}C$, $^{13}N$, $^{15}O$, $^{166}HO$ and $^{18}F$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Ag$, $^{166}HO$ or $^{177}Lu$.

Other anti-tumor agents, e.q., agents active against proliferating cells, are administrable in accordance with the present invention. Exemplary anti-tumor agents include cytokines, such as IL-2, tumor necrosis factor or the like, lectin inflammatory response promoters (selectins), such as L-selectin, E-selectin, P-selectin or the like, and like molecules.

The galactose cluster reagents may be useful for gene delivery to the liver. Oligonucleotide sequences which might be delivered in accordance with this aspect of the present invention include transcriptionally active gene sequences and gene sequences useful in the antisense format as therapeutic agents. Delivery of genes that are transcriptionally active is particularly advantageous as the liver is very metabolic and receives a large volume of cardiac blood flow output. Genes expressed in the liver, transiently or chronically, and secreted into the circulation will readily perfuse the body. Consequently, delivery of oligonucleotide sequences to the liver may serve to alleviate liver disorders, to address poisoning by hepatotoxic agents in hepatocytes by direct chemical detoxification, or may serve as a platform for the production of therapeutic agents to address other circulation-accessible ailments.

Preferred active agents for use in diagnosis or treatment of liver ailments include the following: anti-parasitic agents, worming agents, anti-cholesterol agents, antibacterials, fungal agents, gene sequences, vitamins, sulfhydryls (e.g., cysteine, glutathione), chelates (e.g., DTPA), nicotinamide co-factors (e.g., NADH, NADPH, NAD and NADP) glucocorticoids, alcohol/aldehyde dehydrogenase, acyclovir, vidarabine, interferon-alpha, corticosteroids and the like. Such active agents may be conjugated to hexose clusters of the present invention in accordance with techniques similar to those described herein for alternative conjugations of such clusters. One skilled in the art is capable of accomplishing such conjugation in accordance with the teachings herein.

One embodiment of the present invention involves the preparation and use of bispecific agents for use in clearance of previously administered molecules or toxic or potentially toxic molecules present in a patient's circulation or extravascular fluid space. Previously administered molecules may include active agent-containing conjugates, targeting moiety-receptor conjugates (e.g., monoclonal antibody or fragment-ligand or anti-ligand conjugates) or the like. In this·circumstance, the hepatic-directed molecule of the present invention is employed to clear the previously administered molecule from non-target sites.

Preferred hepatic-directed molecules of the present invention are present in the circulation and are capable of penetrating the extravascular fluid space. Consequently, previously administered compounds that are present in the circulation or in the extravascular fluid space are accessible to hepatic-directed compounds of the present invention. Circulating compounds are removed via association with hepatic-directed compound and removal via liver receptors. Previously administered compounds, present in extravascular fluid space but not associated with a target cell or epitope, are removed via liver receptors as such compounds are diffused back into the circulation in association with hepatic-directed compounds. Residual hepatic-directed compound which may become bound to a targeted agent (targeting moiety-anti-ligand conjugate, for example) should dissociate over time, thereby providing access to the targeted agent for subsequently administered active agent designed to localize thereto.

Toxic or potentially toxic molecules that may be removed from a recipient's circulation or extravascular fluid space include: chemotherapeutics (e.g., alkylators), heavy metals and the like. Binding moieties capable of associating with toxic or potentially toxic molecules resident in the recipient's circulation or extravascular fluid space include antibodies or fragments thereof directed to epitopes that are characteristic of such toxin or potential toxin. Other useful binding moieties include oligonucleotides, any ligands or anti-ligands in pretargeting embodiments of the present invention.

In pretargeting aspects of the present invention wherein the binding moiety is employed to remove a targeting moiety-ligand or anti-ligand conjugate from the recipient's circulation and/or extravascular fluid space, characteristics of useful binding moieties are discussed below. The binding between the binding moiety of the hepatic-directed compounds of the present invention and the molecule to be cleared from the circulation or extravascular fluid space need only be transient, i.e., for a sufficient amount of time to clear the molecule from circulation or extravascular fluid space to the liver. Under these circumstances, the hepatic-directed molecule of the present invention is employed to remove the toxic or potentially toxic molecule from the patient's circulation or extravascular fluid space.

In general, the binding constant characterizing the interaction of the binding moiety of the hepatic-directed compound and the molecule to be bound thereby should be low enough to keep short the residence time of the hepatic-directed moiety at target sites. Also, the binding constant must be sufficiently high to capture the molecule to be bound and traffic that molecule to the liver. Selection of the ideal binding constant for the binding moieties employed in hepatic-directed compounds of the present invention depends upon factors including:

(i) Rate of clearance of the in vivo-associated construct (e.g., monoclonal antibody-anti-ligand-ligand-galactose cluster) by the liver; and (ii) Time before an active agent-containing conjugate is administered (in embodiments of the present invention wherein hepatic-directed compounds are employed to clear previously administered moieties).

With respect to criterion (i), the faster the rate of clearance, the lower (weaker) the binding constant needs to be. With respect to criterion, (ii), the greater the amount of time between administration of the hepatic-directed compound and the active agent-containing conjugate, the greater (stronger) the binding constant can be as more time is available for dissociation of the binding moiety from targeted constructs. For clinical convenience, a relatively short time interval and, therefore, a somewhat weaker binding constant are preferred Binding moieties of the present invention include ligands, anti-ligands, and other target epitope-recognizing moieties. One skilled in the art can substitute acceptable moieties for the binding moieties discussed specifically herein. Preferred binding moieties are characterized by a molecular weight of a Fab fragment of a monoclonal antibody or lower. Such binding moieties may also be modified to include suitable functional groups to allow for attachment of other molecules of interest, e:g., peptides, proteins, nucleotides, and other small molecules.

A recognized disadvantage associated with in vivo administration of targeting moiety-radioisotopic conjugates for imaging or therapy is localization of the attached radioactive agent at both non-target and target sites. Until the administered radiolabeled conjugate clears from the circulation, normal organs and tissues are transitorily exposed to the attached radioactive agent. For instance, radiolabeled whole antibodies that are administered in vivo exhibit relatively slow blood clearance; maximum target site localization generally occurs 1–3 days post-administration. Generally, the longer the clearance time of the conjugate from the circulation, the greater the radioexposure of non-target organs. Therapeutic drugs, administered alone or as targeted conjugates, are accompanied by similar disadvantages.

One method for reducing non-target tissue exposure to a diagnostic or therapeutic agent involves "pretargeting" the targeting moiety at a target site, and then subsequently administering a rapidly clearing diagnostic or therapeutic agent conjugate that is capable of binding to the "pretargeted" targeting moiety at the target site. A description of some embodiments of the pretargeting technique may be found in U.S. Pat. No. 4,863,713 (Goodwin et al.).

"Two-step" pretargeting procedures feature targeting moiety-ligand or targeting moiety-anti-ligand administration, followed by administration of active agent conjugated to the opposite member of the ligand-anti-ligand pair. As an optional step "1.5" in the two-step pretargeting methods of the present invention, a clearing agent (preferably other than ligand or anti-ligand alone) is administered to facilitate the clearance of circulating targeting moiety-containing conjugate.

In the two-step pretargeting approach, the clearing agent preferably does not become bound to the target cell population, either directly or through the previously administered and target cell bound targeting moiety-anti-ligand or targeting moiety-ligand conjugate. An example of two-step pretargeting involves the use of biotinylated human transferrin as a clearing agent for avidin-targeting moiety conjugate, wherein the size of the clearing agent results in liver clearance of transferrin-biotin-circulating avidin-targeting moiety complexes and substantially precludes association with the avidin-targeting moiety conjugates bound at target cell sites. (See, Goodwin, D. A., Antibod. Immunoconi. Radiopharm., 4: 427–34, 1991).

Ligands suitable for use within the present invention include biotin, haptens, lectins, epitopes, dsDNA fragments, enzyme inhibitors and analogs and derivatives thereof. Useful complementary anti-ligands include avidin (for biotin), carbohydrates (for lectins) and antibody, fragments or analogs thereof, including mimetics (for haptens and epitopes) and zinc finger proteins (for dsDNA fragments) and enzymes (for enzyme inhibitors). Preferred ligands and anti-ligands bind to each other with an affinity of at least about $k_D$ $10^9$M. Other useful ligand/anti-ligand systems include S-protein/S-peptide, head activator protein (which binds to itself), cystatin-C/cathepsin B, and the like.

One preferred chelate system for use in the practice of the present invention is based upon a 1,4,7,10-tetraazacyclododecane-N, N', N", N'"-tetra acetic acid (DOTA) construct. Because DOTA strongly binds Y-90 and other radionuclides, it has been proposed for use in radioimmunotherapy. For therapy, it is very important that the radionuclide be stably bound within the DOTA chelate and that the DOTA chelate be stably attached to an effector, such as a ligand or an anti-ligand.

The strategy for design of the DOTA-containing molecules and conjugates for use in the practice of embodiments of the present invention wherein the effector is biotin involved three primary considerations:

1) in vivo stability (including biotinidase and general peptidase activity resistance), with an initial acceptance criterion of 100% stability for 1 hour;

2) renal excretion; and 3) ease of synthesis.

The same or similar criteria are applicable to alternative effectors, as can be readily ascertained by one of ordinary skill in the art.

The DOTA-biotin conjugates that are preferably employed in the practice of the present invention reflect the implementation of one or more of the following strategies:

1) substitution of the carbon adjacent to the cleavage susceptible amide nitrogen;

2) alkylation of the cleavage susceptible amide nitrogen;

3) substitution of the amide carbonyl with an alkyl amino group;

4) incorporation of D-amino acids as well as analogs or derivatives thereof; or 5) incorporation of thiourea linkages.

DOTA-biotin conjugates in accordance with the present invention are described in published PCT Patent Application No. PCT/US93/05406. Methods of preparing preferred embodiments of DOTA-biotin conjugates are described in Example III hereof.

The preferred linkers are useful to produce DOTA-biotin or other DOTA-small molecule, conjugates having one or more of the following advantages:

bind avidin or streptavidin with the same or substantially similar affinity as free biotin;

bind metal $M^{+3}$ ions efficiently and with high kinetic stability;

are excreted primarily through the kidneys into urine;

are stable to endogenous enzymatic or chemical degradation (e.g., bodily fluid amidases, peptidases or the like);

penetrate tissue rapidly and bind to pretargeted avidin or streptavidin; and are excreted rapidly with a whole body residence half-life of less than about 5 hours.

One component to be administered in a preferred two-step pretargeting protocol is a targeting moiety-anti-ligand or a targeting moiety-ligand conjugate. Streptavidin-proteinaceous targeting moiety conjugates are preferably prepared as described in Example II below, with the preparation involving the steps of: preparation of SMCC-derivitized streptavidin; preparation of DTT-reduced proteinaceous targeting moiety; conjugation of the two prepared moieties; and purification of the monosubstituted or disubstituted (with respect to streptavidin) conjugate from crosslinked (antibody-streptavidin-antibody) and aggregate species and unreacted starting materials. The purified fraction is preferably further characterized by one or more of the following techniques: HPLC size exclusion, SDS-PAGE, immunoreactivity, biotin binding capacity and in vivo studies.

One embodiment of the present invention provides clearing agents having physical properties facilitating use for in vivo complexation and blood clearance of anti-ligand/ligand (e.g., avidin/biotin)-targeting moiety (e.g., antibody) conjugates. These clearing agents are useful in improving the target:blood ratio of targeting moiety conjugate.

Other applications of these clearing agents include lesional imaging or therapy involving blood clots and the like, employing antibody or other targeting vehicle-active agent delivery modalities. For example, efficacious anti-clotting agent provides rapid target localization and high target:non-target targeting ratio. Active agents administered in pretargeting protocols of the present invention using efficient clearing agents are targeted in the desirable manner and are, therefore, useful in the imaging/therapy of conditions such as pulmonary embolism and deep vein thrombosis.

Clearing agents useful in the practice of the present invention preferably exhibit one or more of the following characteristics:

rapid, efficient complexation with targeting moiety-ligand (or anti-ligand) conjugate in vivo;

rapid clearance from the blood of targeting moiety conjugate capable of binding a subsequently administered complementary anti-ligand or ligand containing molecule;

high capacity for clearing (or inactivating) large amounts of targeting moiety conjugate; and low immunogenicity.

Preferred clearing agents include sugar cluster-bearing moieties. The sugars employed in such clusters are preferably hexoses. Such hexose cluster-bearing clearing agents are molecules that have been derivatized to incorporate a cluster of three or more hexoses (six carbon sugar moieties) recognized by Ashwell receptors or other receptors such as the mannose/N-acetylglucosamine receptor which are associated with endothelial cells and/or Kupffer cells of the liver or the mannose 6-phosphate receptor. Exemplary of such hexoses are galactose, mannose, mannose 6-phosphate, N-acetylglucosamine, pentamannosylphosphate, and the like. Other moieties recognized by Ashwell receptors, including glucose, N-galactosamine, N-acetylgalactosamine, pentamannosyl phosphate, thioglycosides of galactose and, generally, D-galactosides and glucosides or the like may also be used in the practice of the present invention. Galactose is the prototypical clearing agent hexose derivative for the purposes of this description.

Exposed galactose residues of the galactose cluster direct the clearing agent to rapid clearance by endocytosis into the liver through specific receptors therefor (Ashwell receptors). These receptors bind the clearing agent, and induce endocytosis into the hepatocyte, leading to fusion with a lysosome and recycle of the receptor back to the cell surface. This clearance mechanism is characterized by high efficiency, high capacity and rapid kinetics.

Clearing agents previously developed incorporated human serum albumin (HSA) as follows:

(Hexose)$_m$—Human Serum Albumin (HSA)—(Ligand)$_n$, wherein n is an integer from 1 to about 10 and m is an integer from 1 to about 45 and wherein the hexose is recognized by Ashwell receptors.

The galactose cluster-bearing clearing agents of the present invention are preferably capable of (1) rapidly and efficiently complexing with the relevant ligand- or anti-ligand-containing conjugates via ligand-anti-ligand affinity; and (2) clearing such complexes from the blood via the galactose receptor, a liver specific degradation system, as opposed to aggregating into complexes that are taken up by the generalized RES system, including the lung and spleen. Additionally, the rapid kinetics of galactose-mediated liver uptake, coupled with the affinity of the ligand-anti-ligand interaction, allow the use of intermediate or even low molecular weight carriers.

Clearing agent evaluation experimentation involving galactose- and biotin-derivatized clearing agents is detailed in Example IV. The specific clearing agent examined during the Example IV experimentation are human serum albumin derivatized with galactose and biotin and a 70,000 dalton molecular weight dextran derivatized with both biotin and galactose. The experimentation showed that proteins and polymers are derivatizable to contain both galactose and biotin and that the resultant derivatized molecule is effective in removing circulating streptavidin-protein conjugate from the serum of the recipient. Biotin loading was varied to determine the effects on both clearing the blood pool of circulating avidin-containing conjugate and the ability to deliver a subsequently administered biotinylated isotope to a target site recognized by the streptavidin-containing conjugate. The effect of relative doses of the administered components with respect to clearing agent efficacy was also examined. Experimentation comparing such clearing agents to those hexose cluster-bearing moieties of the present invention is set forth in Example VI below.

The small molecule clearing agents are superior to the proteinaceous clearing agents from cost, regulatory and characterization perspectives. More specifically, the small molecule clearing agents are preparable from available or easily synthesizable components and are amenable to more precise characterization. In addition, if biotin release from the proteinaceous clearing agent is determined to be problematic, such release can be avoided or the impact of such release minimized using a small molecule clearing agent incorporating a highly stable biotin linker or incorporating a lower affinity biotin analog, respectively.

The present invention provides sugar cluster-bearing clearing agents that incorporate ligand derivatives or anti-ligand derivatives, wherein such derivatives exhibit a lower affinity for the complementary ligand/anti-ligand pair member than the native form of the compound (i.e., lower affinity ligands or anti-ligands). In embodiments of the present invention employing a biotin-avidin or biotin-streptavidin ligand/anti-ligand pair, preferred sugar cluster-bearing clearing agents incorporate either lower affinity biotin (which exhibits a lower affinity for avidin or streptavidin than native biotin) or lower affinity avidin or a streptavidin (which exhibits a lower affinity for biotin than native avidin or streptavidin).

Sugar cluster-bearing clearing agents that employ a ligand or anti-ligand moiety that is complementary to the ligand/anti-ligand pair member (previously administered in conjunction with the targeting moiety) are useful in the practice of the present invention. When such clearing agents localize to hepatocytes, they are generally rapidly degraded. This degradation liberates a quantity of free ligand or free anti-ligand into the circulation. This bolus release of ligand or anti-ligand may compete for binding sites of targeting moiety-ligand or targeting moiety-anti-ligand with subsequently administered active agent-ligand or active agent-anti-ligand conjugate.

This competition can be addressed by using a sugar cluster-bearing clearing agent incorporating a lower affinity ligand or anti-ligand. In other words, the ligand or anti-ligand employed in the structure of the clearing agent more weakly binds to the complementary ligand/anti-ligand pair member than native ligand or anti-ligand. Consequently, lower affinity ligand or anti-ligand derivatives that bind to target-localized targeting moiety-anti-ligand or targeting moiety-ligand conjugate may be displaced by the subsequently administered, active agent-native (or higher binding affinity ligand) or active agent-native (or higher binding affinity) anti-ligand conjugate.

In two-step pretargeting protocols employing the biotin-avidin or biotin-streptavidin ligand-anti-ligand pair, lower affinity biotin, lower affinity avidin or lower affinity streptavidin may be employed. Exemplary lower affinity biotin molecules, for example, exhibit the following properties: bind to avidin or streptavidin with an affinity less than that of native biotin ($10^{-15}$); retain specificity for binding to avidin or streptavidin; are non-toxic to mammalian recipients; and the like. Exemplary lower affinity avidin or streptavidin molecules, for example, exhibit the following properties: bind to biotin with an affinity less than native avidin or streptavidin; retain specificity for binding to biotin; are non-toxic to mammalian recipients; and the like.

Exemplary lower affinity biotin molecules include 2'-thiobiotin; 2'-iminobiotin; 1'-N-methoxycarbonyl-biotin; 3'-N-methoxycarbonylbiotin; 1-oxy-biotin; 1-oxy-2'-thiobiotin; 1-oxy-2'-iminobiotin; 1-sulfoxide-biotin; 1-sulfoxide-2'-thiobiotin; 1-sulfoxide-2'iminobiotin; 1-sulfone-biotin; 1-sulfone-2'-thio-biotin; 1-sulfone-2'-iminobiotin; imidazolidone derivatives such as desthiobiotin (d and dl optical isomers), dl-desthiobiotin methyl ester, dl-desthiobiotinol, D-4-n-hexyl-imidazolidone, L-4-n-hexylimidazolidone, dl-4-n-butyl-imidazolidone, dl-4-n-propylimidazolidone, dl-4-ethyl-imidazolidone, dl-4-methylimidazolidone, imidazolidone, dl-4,5-dimethylimidazolidone, meso-4,5-dimethylimidazolidone, dl-norleucine hydantoin, D-4-n-hexyl-2-thionoimidazolidine, d-4-n-hexyl-2-imino-imidazolidine and the like; oxazolidone derivatives such as D-4-n-hexyloxazolidone, D-5-n-hexyloxazolidone and the like; [5-(3,4-diamino-thiophan-2-yl] pentanoic acid; lipoic acid; 4-hydroxy-azobenzene-2'-carboxylic acid; and the like. Preferred lower affinity biotin molecules for use in the practice of the present invention are 2'-thiobiotin, desthiobiotin, 1-oxy-biotin, 1-oxy-2'-thiobiotin, 1-sulfoxide-biotin, 1-sulfoxide-2'-thiobiotin, 1-sulfone-biotin, 1-sulfone-2'-thiobiotin, lipoic acid and the like. These exemplary lower affinity biotin molecules may be produced substantially in accordance with known procedures therefor. Conjugation of the exemplary lower affinity biotin molecules to sugar cluster directors proceeds substantially in accordance with procedures described herein in regard to biotin conjugation.

Much has been reported about the binding affinity of different biotin analogs to avidin. Based upon what is known in the art, the ordinary skilled artisan could readily select or use known techniques to ascertain the respective binding affinity of a particular biotin analog to streptavidin, avidin or a derivative thereof.

The present invention further provides methods of increasing active agent localization at a target cell site of a mammalian recipient, which methods include:
administering to the recipient a first conjugate comprising a targeting moiety and a member of a ligand-anti-ligand binding pair;
thereafter administering to the recipient a clearing agent bearing a sugar cluster capable of directing the clearance of circulating first conjugate via hepatocyte receptors of the recipient, wherein the clearing agent incorporates lower affinity complementary member of the ligand-anti-ligand binding pair; and
subsequently administering to the recipient a second conjugate comprising an active agent and a ligand/anti-ligand binding pair member, wherein the second conjugate binding pair member is complementary to that of the first conjugate and, preferably, constitutes a native or high affinity form of the member.

Clearing agents of the present invention may be administered in single or multiple doses or via continuous infusion. A single dose of biotinylated clearing agent, for example, produces a rapid decrease in the level of circulating targeting moiety-streptavidin, followed by a small increase in that level, presumably caused, at least in part, by re-equilibration of targeting moiety-streptavidin within the recipient's physiological compartments. A second or additional clearing agent doses may then be employed to provide supplemental clearance of targeting moiety-streptavidin. Alternatively, clearing agent may be infused intravenously for a time period sufficient to clear targeting moiety-streptavidin in a continuous manner.

Other types of clearing agents and clearance systems are also useful in the practice of the present invention to remove circulating targeting moiety-ligand or -anti-ligand conjugate from the recipient's circulation. Particulate-based clearing agents, for example, are discussed in Example I. Such particulate-based clearing agents can be employed in conjunction with sugar clusters to provide hepatic-directed compounds of the present invention.

One embodiment of the present invention in which rapid acting sugar cluster director-bearing clearing agents are useful is in the delivery of Auger emitters, such as I-125, I-123, Er-165, Sb-119, Hg-197, Ru-97, Tl-201 and I-125 and Br-77, or nucleus-binding drugs to target cell nuclei. In these embodiments of the present invention, targeting moieties that localize to internalizing receptors on target cell surfaces are employed to deliver a targeting moiety-containing conjugate (i.e., a targeting moiety-anti-ligand conjugate in the preferred two-step protocol) to the target cell population. Such internalizing receptors include EGF receptors, transferrin receptors, HER2 receptors, IL-2 receptors, other interleukins and cluster differentiation receptors, somatostatin receptors, other peptide binding receptors and the like.

After the passage of a time period sufficient to achieve localization of the conjugate to target cells, but insufficient to induce internalization of such targeted conjugates by those cells through a receptor-mediated event, a rapidly acting sugar cluster director-bearing clearing agent is administered. In a preferred two-step protocol, an active agent-containing ligand or anti-ligand conjugate, such as a biotin-Auger. emitter or a biotin-nucleus acting drug, is administered as soon as the clearing agent has been given an opportunity to complex with circulating targeting moiety-containing conjugate, with the time lag between clearing agent and active agent administration being less than about 24 hours. In this manner, active agent is readily internalized through target cell receptor-mediated internalization. While circulating Auger emitters are thought to be non-toxic, the rapid, specific targeting afforded by the pretargeting protocols of the present invention increases the potential of shorter half-life Auger emitters, such as I-123, which is available and capable of stable binding.

The invention is further described through presentation of the following examples. These examples are offered by way of illustration, and not by way of limitation.

dosage form through covalent or non-covalent modalities as set forth herein to provide accessible ligand or anti-ligand for binding to its previously administered circulating binding pair member.

Preferable particulate clearing agents of the present invention are biodegradable or non-biodegradable microparticulates. More preferably, the particulate clearing agents are formed of a polymer containing matrix that biodegrades by random, nonenzymatic, hydrolytic scissioning.

Polymers derived from the condensation of alpha hydroxycarboxylic acids and related lactones are more preferred for use in the present invention. A particularly preferred moiety is formed of a mixture of thermoplastic polyesters (e.g., polylactide or polyglycolide) or a copolymer of lactide and glycolide components, such as poly(lactide-co-glycolide). An exemplary structure, a random poly(DL-lactide-co-glycolide), is shown.below, with the values of x and y being manipulable by a practitioner in the art to achieve desirable microparticulate properties.

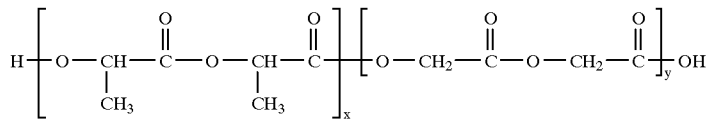

EXAMPLE I

Particulate Clearing Agents

Clearance of chimeric monoclonal antibody-avidin is facilitated by administration of a particulate-type clearing agent (e.g., a polymeric particle having a plurality of biotin molecules bound thereto). Such a particulate clearing agent preferably constitutes a biodegradable polymeric carrier having a plurality of biotin molecules bound thereto. Particulate clearing agents of the present invention exhibit the capability of binding to circulating administered conjugate and removing that conjugate from the recipient. Particulate clearing agents of this aspect of the present invention may be of any configuration suitable for this purpose. Preferred particulate clearing agents exhibit one or more of the following characteristics:

- microparticulate (e.g., from about 0.5 micrometers to about 100 micrometers in diameter, with from about 0.5 to about 2 micrometers more preferred), free flowing powder structure;
- biodegradable structure designed to biodegrade over a period of time between from about 3 to about 180 days, with from about 10 to about 21 days more preferred, or non-biodegradable structure;
- biocompatible with the recipients physiology over the course of distribution, metabolism and excretion of the clearing agent, more preferably including biocompatible biodegradation products;
- and capability to bind with one or more circulating conjugates to facilitate the elimination or removal thereof from the recipient through one or more binding moieties (preferably, the complementary member of the ligand/anti-ligand pair). The total molar binding capacity of the particulate clearing agents depends upon the particle size selected and the ligand or anti-ligand substitution ratio. The binding moieties are capable of coupling to the surface structure of the particulate Other agents suitable for forming particulate clearing agents of the present invention include polyorthoesters and polyacetals (*Polymer Letters*, 18:293, 1980) and polyorthocarbonates (U.S. Pat. No. 4,093,709) and the like.

Preferred lactic acid/glycolic acid polymer containing matrix particulates of the present invention are prepared by emulsion-based processes, that constitute-modified solvent extraction processes such as those described by Cowsar et al., "Poly(Lactide-Co-Glycolide) Microcapsules for Controlled Release of Steroids," *Methods Enzymolocy*, 112:101–116, 1985 (steroid entrapment in microparticulates); Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity*, 59:2978–2986, 1991 (toxoid entrapment); Cohen et al., "Controlled Delivery Systems for Proteins Based on Poly(Lactic/Glycolic Acid) Microspheres," *Pharmaceutical Research*, 8(6):713–720, 1991 (enzyme entrapment); and Sanders et al., "Controlled Release of a Luteinizing Hormone-Releasing Hormone Analogue from Poly(D,L-Lactide-Co-Glycolide) Microspheres," *J. Pharmaceutical Science*, 73(9):1294–1297, 1984 (peptide entrapment).

In general, the procedure for forming particulate clearing agents of the present invention involves dissolving the polymer in a halogenated hydrocarbon solvent and adding an additional agent that acts as a solvent for the halogenated hydrocarbon solvent but not for the polymer. The polymer precipitates out from the polymer-halogenated hydrocarbon solution. Following particulate formation, they are washed and hardened with an organic solvent. Water washing and aqueous non-ionic surfactant washing steps follow, prior to drying at room temperature under vacuum.

For biocompatibility purposes, particulate clearing agents are sterilized prior to packaging, storage or administration. Sterilization may be conducted in any convenient manner therefor. For example, the particulates can be irradiated with gamma radiation, provided that exposure to such radiation does not adversely impact the structure or function of the binding moiety attached thereto. If the binding moiety is so adversely impacted, the particulate clearing agents can be produced under sterile conditions.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for binding moiety-particulate bonding, are optionally included in the particulate structure, along with the non-degradable or biodegradable polymeric units. Functional groups that are exploitable for this purpose include those that are reactive with ligands or anti-ligands and hexose cluster director reagents, such as carboxyl groups, amine groups, sulfhydryl groups and the like. Preferred binding enhancement moieties include the terminal carboxyl groups of the preferred (lactide-glycolide) polymer containing matrix or the like. A practitioner in the art is capable of selecting appropriate functional groups and monitoring conjugation reactions involving those functional groups.

Advantages garnered through the use of particulate clearing agents of the type described above are as follows:

particles in the "micron" size range localize in the RES and liver, with galactose derivatization or charge modification enhancement methods for this capability available, and, preferably, are designed to remain in circulation for a time sufficient to perform the clearance function;

the size of the particulates facilitates central vascular compartment retention thereof, substantially precluding equilibration into the peripheral or extravascular compartment;

desired substituents for ligand or anti-ligand binding to the particulates can be introduced into the polymeric structure;

ligand- or anti-ligand-particulate linkages having desired properties (e.g., serum biotinidase resistance thereby reducing the release of biotin metabolite from a particle-biotin clearing agent) and multiple ligands or anti-ligands can be bound to the particles to achieve optimal cross-linking of circulating targeting agent-ligand or -anti-ligand conjugate and efficient clearance of cross-linked species. This advantage is best achieved when care is taken to prevent particulate aggregation both in storage and upon in vivo administration.

EXAMPLE II

Targeting Moiety-Anti-Ligand Conjugate for Two-Step Pretargeting In Vivo

A. Preparation of SMCC-Derivitized Streltavidin.

31 mg (0.48 mol) streptavidin was dissolved in 9.0 ml PBS to prepare a final solution at 3.5 mg/ml. The pH of the solution was adjusted to 8.5 by addition of 0.9 ml of 0.5 M borate buffer, pH 8.5. A DMSO solution of SMCC (3.5 mg/ml) was prepared, and 477 1 (4.8 mol) of this solution was added dropwise to the vortexing protein solution. After 30 minutes of stirring, the solution was purified by G-25 (PD-10, Pharmacia, Picastaway, N.J.) column chromatography to remove unreacted or hydrolyzed SMCC. The purified SMCC-derivitized streptavidin was isolated (28 mg, 1.67 mg/ml).

B. Preparation of DTT-Reduced NR-LU-10.

To 77 mg NR-LU-10 (0.42 mol) in 15.0 ml PBS was added 1.5 ml of 0.5 M borate buffer, pH 8.5. A DTT solution, at 400 mg/ml (165 1) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

C. Coniugation of SMCC-Streptavidin to DTT-Reduced NR-LU-10.

DTT-reduced NR-LU-10 (63 mg, 29 ml, 0.42 mol) was diluted with 44.5 ml PBS. The solution of SMCC-streptavidin (28 mg, 17 ml, 0.42 mol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

D. Purification of Conjugate.

For small scale reactions, monosubstituted or disubstituted (with regard to streptavidin) conjugate was obtained using HPLC Zorbax (preparative) size exclusion chromatography. The desired monosubstituted or disubstituted conjugate product eluted at 14.0–14.5 min (3.0 ml/min flow rate), while unreacted NR-LU-10 eluted at 14.5–15 min and unreacted derivitized streptavidin eluted at 19–20 min.

For larger scale conjugation reactions, monosubstituted or disubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increasing salt gradient in 20 mM diethanolamine adjusted to pH 8.6 with sodium hydroxide.

E. Characterization of Coniugate.

1. HPLC size exclusion was conducted as described above with respect to small scale purification.

2. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di- substituted conjugates.

3. Immunoreactivity was assessed, for example, by competitive binding ELISA as compared to free antibody. Values obtained were within 10% of those for the free antibody.

4. Biotin binding capacity was assessed, for example, by titrating a known quantity of conjugate with p-[I-125] iodobenzoylbiocytin. Saturation of the biotin binding sites was observed upon addition of 4 equivalences of the labeled biocytin.

5. In vivo studies are useful to characterize the reaction product, which studies include, for example, serum clearance profiles, ability of the conjugate to target antigen-positive tumors, tumor retention of the conjugate over time and the ability of a biotinylated molecule to bind streptavidin conjugate at the tumor.

These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

For example, FIG. 1 depicts the tumor.uptake profile of the NR-LU-10-streptavidin conjugate (LU-10-StrAv) in comparison to a control profile of native NR-LU-10 whole antibody. LU-10-StrAv was radiolabeled on the streptavidin component only, giving a clear indication that LU-10-StrAv localizes to target cells as efficiently as NR-LU-10 whole antibody itself.

EXAMPLE III

Synthesis of DOTA-Biotin Conjugates

A. Synthesis of Nitro-Benzyl-DOTA.

The synthesis of aminobenzyl-DOTA was conducted substantially in accordance with the procedure of McMurry et al., *Bioconlurate Chem.*, 3: 108–117, 1992. The critical step in the prior art synthesis is the intermolecular cyclization between disuccinimidyl N-(tert-butoxycarbonyl) iminodiacetate and N-(2-aminoethyl)-4-nitrophenyl alaninamide to prepare 1-(tert-butoxycarbonyl)-5-(4-nitrobenzyl)-3,6,11-trioxo-1,4,7,10-tetraazacyclododecane. In other words, the critical step is the intermolecular cyclization between the bis-NHS ester and the diamine to give the cyclized dodecane. McMurry et al. conducted the cyclization step on a 140 mmol scale, dissolving each of the reagents in 100 ml DMF and adding via a syringe pump over 48 hours to a reaction pot containing 4 liters dioxane.

A 5× scale-up of the McMurry et al. procedure was not practical in. terms of reaction volume, addition rate and reaction time. Process chemistry studies revealed that the reaction addition rate could be substantially increased and that the solvent volume could be greatly reduced, while still obtaining a similar yield of the desired cyclization product. Consequently on a 30 mmol scale, each of the reagents was dissolved in 500 ml DMF and added via addition funnel over 27 hours to a reaction pot containing 3 liters dioxane. The addition rate of the method employed involved a 5.18 mmol/hour addition rate and a 0.047 M reaction concentration.

B. Synthesis of an N-methyl-alvcine Linked Conlucate.

The N-methyl glycine-linked DOTA-biotin conjugate was prepared by an analogous method to that used to prepare D-alanine-linked DOTA-biotin conjugates. N-methylglycine (trivial name sarcosine, available from Sigma Chemical Co.) was condensed with biotin-NHS ester in DMF and triethylamine to obtain N-methyl glycyl-biotin. N-methyl-glycyl biotin was then activated with EDCI and NHS. The resultant NHS ester was not isolated and was condensed in situ with DOTA-aniline and excess pyridine. The reaction solution was heated at 60° C. for 10 minutes and then evaporated. The residue was purified by preparative HPLC to give [(N-methyl-N-biotinyl)-N-glycyl]-aminobenzyl-DOTA.

1. Preparation of (N-methyl)glycyl biotin. DMF (8.0 ml) and triethylamine (0.61 ml, 4.35 mmol) were added to solids N-methyl glycine (182 mg, 2.05 mmol) and N-hydroxysuccinimidyl biotin (500 mg, 1.46 mmol). The mixture was heated for 1 hour in an oil bath at 85° C. during which time the solids dissolved producing a clear and colorless solution. The solvents were then evaporated. The yellow oil residue was acidified with glacial acetic acid, evaporated and chromatographed on a 27 mm column packed with 50 g silica, eluting with 30% MeOH/EtOAc 1% HOAc to give the product as a white solid (383 mg) in 66% yield.

H-NMR (DMSO): 1.18–1.25 (m, 6H, $(CH_2)_3$), 2.15, 2.35 (2 t's, 2H, $CH_2CO$), 2.75 (m, 2H, $SCH_2$), 2.80, 3.00 (2 s's, 3H, $NCH_3$), 3.05–3.15 (m, 1H, SCH), 3.95, 4.05 (2 s's, 2H, $CH_2N$), 4.15, 4.32 (2 m's, 2H, 2CHN's), 6.35 (s, NH), 6.45 (s, NH).

2. Preparation of [(N-methyl-N-biotinyl)glycyl] aminobenzyl-DOTA. N-hydroxysuccinimide (10 mg, 0.08 mmol) and EDCI (15 mg, 6.08 mmol) were added to a solution of (N-methylglycyl) biotin (24 mg, 0.08 mmol) in DMF (1.0 ml). The solution was stirred at 23° C. for 64 hours. Pyridine (0.8 ml) and aminobenzyl-DOTA (20 mg, 0.04 mmol) were added. The mixture was heated in an oil bath at 63° C. for 10 minutes, then stirred at 23° C. for 4 hours. The solution was evaporated. The residue was purified by preparative HPLC to give the product as an off white solid (8 mg, 0.01 mmol) in 27% yield.

H-NMR ($D_2O$): 1.30–1.80 (m, 6H), 2.40, 2.55 (2 t's, 2H, $CH_2CO$), 2.70–4.2 (complex multiplet), 4.35 (m, CHN), 4.55 (m, CHN), 7.30 (m, 2H, benzene hydrogens), 7.40 (m, 2H, benzene hydrogens).

EXAMPLE IV

Clearing Agent Evaluation Experimentation

A. Galactose- and Biotin-Derivatization of Human Serum Albumin (HSA).

HSA was evaluated because it exhibits the advantages of being both inexpensive and non-immunogenic. HSA was derivatized with varying levels of biotin (1-about 9 biotins/molecule) via analogous chemistry to that previously described with respect to AO. More specifically, to a solution of HSA available from Sigma Chemical Co. (5–10 mg/ml in PBS) was added 10% v/v 0.5M sodium borate buffer, pH 8.5, followed by dropwise addition of a DMSO solution of NHS-LC-biotin (Sigma Chemical Co.) to the stirred solution at the desired molar offering (relative molar equivalents of reactants). The final percent DMSO in the reaction mixture should not exceed 5%. After stirring for 1 hour at room temperature, the reaction was complete. A 90% incorporation efficiency for biotin on HSA was generally observed. As a result, if 3 molar equivalences of the NHS ester of LC-biotin was introduced, about 2.7 biotins per HSA molecule were obtained. Unreacted biotin reagent was removed from the biotin-derivatized HSA using G-25 size exclusion chromatography. Alternatively, the crude material may be directly galactosylated. The same chemistry is applicable for biotinylating- non-previously biotinylated dextran.

HSA-biotin was then derivatized with from 12 to 45 galactoses/molecule. Galactose derivatization of the biotinylated HSA was performed according to the procedure of Lee, et al., *Biochemistry*, 15: 3956, 1976. More specifically, a 0.1M methanolic solution of cyanomethyl-2,3,4,6-tetra-O-acetyl-1-thio-D-galactopyranoside was prepared and reacted with a 10% v/v 0.1M NaOMe in methanol for 12 hours to generate the reactive galactosyl thioimidate. The galactosylation of biotinylated HSA began by initial evaporation of the anhydrous methanol from a 300 fold molar excess of reactive thioimidate. Biotinylated HSA in PBS, buffered with 10% v/v 0.5M sodium borate, was added to the oily residue. After stirring at room temperature for 2 hours, the mixture was stored at 4° C. for 12 hours. The galactosylated HSA-biotin was then purified by G-25 size exclusion chromatography or by buffer,exchange to yield the desired product. The same chemistry is exploitable to galactosylating dextran. The incorporation efficiency of galactose on HSA is approximately 10%.

70 micrograms of Galactose-HSA-Biotin (G-HSA-B), with 12–45 galactose residues and 9 biotins, was administered to mice which had been administered 200 micrograms of StrAv-MAb or 200 microliters of PBS 24 hours earlier. Results indicated that G-HSA-B is effective in removing StrAv-MAb from circulation. Also, the pharmacokinetics of G-HSA-B is unperturbed and rapid in the presence or absence of circulating MAb-StrAv.

B. Non-Protein Clearing Agent.

A commercially available form of dextran, molecular weight of 70,000 daltons, pre-derivatized with approximately 18 biotins/molecule and having an equivalent number of free primary amines was studied. The primary aminie moieties were derivatized with a galactosylating reagent, substantially in accordance with the procedure therefor described above in the discussion of HSA-based clearing agents, at a level of about 9 galactoses/molecule. The molar equivalence offering ratio of galactose to HSA was about 300:1, with about one-third of the galactose being converted to active form. 40 Micrograms of galactose-dextran-biotin (GAL-DEX-BT) was then injected i.v. into one group of mice which had received 200 micrograms MAb-StrAv conjugate intravenously 24 hours earlier, while 80 micrograms of GAL-DEX-BT was injected into other such mice. GAL-DEX-BT was rapid and efficient at clearing StrAv-MAb conjugate, removing over 66% of circulating conjugate in less than 4 hours after clearing agent administration. An equivalent effect was seen at both clearing agent doses, which correspond to 1.6 (40 micrograms) and 3.2 (80 micrograms) times the stoichiometric amount of circulating StrAv conjugate present.

C. Dose Ranginc for G-HSA-B Clearing Agent.

Dose ranging studies followed the following basic format:
200 micrograms MAb-StrAv conjugate administered;
24 hours later, clearing agent administered; and
2 hours later, 5.7 micrograms PIP-biocytin administered.

Dose ranging studies were performed with the G-HSA-B clearing agent, starting with a loading of 9 biotins per molecule and 12–45 galactose residues per molecule. Doses of 20, 40, 70 and 120 micrograms were administered 24 hours after a 200 microgram dose of MAb-StrAv conjugate. The clearing agent administrations were followed 2 hours later by administration of 5.7 micrograms of I-131-PIP-biocytin. Tumor uptake and blood retention of PIP-biocytin was examined 44 hours after administration thereof (46 hours after clearing agent administration). The results showed that a nadir in blood retention of PIP-biocytin was achieved by all doses greater than or equal to 40 micrograms of G-HSA-B. A clear, dose-dependent decrease in tumor binding of PIP-biocytin at each increasing dose of G-HSA-B was present, however. Since no dose-dependent effect on the localization of MAb-StrAv conjugate at the tumor was observed, this data was interpreted as being indicative of relatively higher blocking of tumorassociated MAb-StrAv conjugate by the release of biotin from catabolized clearing agent. Similar results to those described earlier for the asialoorosomucoid clearing agent regarding plots of tumor/blood ratio were found with respect to G-HSA-B, in that an optimal balance between blood clearance and tumor retention occurred around the 40 microgram dose.

Because of the relatively large molar amounts of biotin that could be released by this clearing agent at higher doses, studies were undertaken to evaluate the effect of lower levels of biotinylation on the effectiveness of the clearing agent. G-HSA-B, derivatized with either 9, 5 or 2 biotins/molecule, was able to clear MAb-StrAv conjugate from blood at equal protein doses of clearing agent. All levels of biotinylation yielded effective, rapid clearance of MAb-StrAv from blood.

Comparison of these 9-, 5-, and 2-biotin-derivatized clearing agents with a single biotin G-HSA-B clearing agent was carried out in tumored mice, employing a 60 microgram dose of each clearing agent. This experiment showed each clearing agent to be substantially equally effective in blood clearance and tumor retention of MAb-StrAv conjugate 2 hours after clearing agent administration. The G-HSA-B with a single biotin was examined for the ability to reduce binding of a subsequently administered biotinylated small molecule (PIP-biocytin) in blood, while preserving tumor binding of PIP-biocytin to prelocalized MAb-StrAv conjugate. Measured at 44 hours following PIP-biocytin administration, tumor localization of both the MAb-StrAv conjugate and PIP-biocytin was well preserved over a broad dose range of G-HSA-B with one biotin/molecule (90 to 180 micrograms). A progressive decrease in blood retention of PIP-biocytin was achieved by increasing doses of the single biotin G-HSA-B clearing agent, while tumor localization remained essentially constant, indicating that this clearing agent, with a lower level of biotinylation, is preferred. This preference arises because the single biotin G-HSA-B clearing agent is both effective at clearing MAb-StrAv over a broader range of doses (potentially eliminating the need for patient-to-patient titration of optimal dose) and appears to release less competing biotin into the systemic circulation than the same agent having a higher biotin loading level.

Another way in which to decrease the effect of clearing agent-released biotin on active agent-biotin conjugate binding to prelocalized targeting moiety-streptavidin conjugate is to attach the protein or polymer or other primary clearing agent component to biotin using a retention linker. A retention linker has a chemical structure that is resistant to agents that cleave peptide bonds and, optionally, becomes protonated when localized to a catabolizing space, such as a lysosome. Preferred retention linkers of the present invention are short strings of D-amino acids or small molecules having both of the characteristics set forth above. An exemplary retention linker of the present invention is cyanuric chloride, which may be interposed between an epsilon amino group of a lysine of a proteinaceous primary clearing agent component and an amine moiety of a reduced and chemically altered biotin carboxy moiety (which has been discussed above) to form a compound of the structure set forth below.

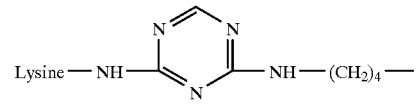

When the compound shown above is catabolized in a catabolizing space, the heterocyclic ring becomes protonated. The ring protonation prevents the catabolite from exiting the lysosome. In this manner, biotin catabolites containing the heterocyclic ring are restricted to the site(s) of catabolism and, therefore, do not compete with active-agent-biotin conjugate for prelocalized targeting moiety-streptavidin target sites.

Comparisons of tumor/blood localization of radiolabeled PIP-biocytin observed in the G-HSA-B dose ranging studies showed that optimal tumor to background targeting was achieved over a broad dose range (90 to 180 micrograms), with the results providing the expectation that even larger clearing agent doses would also be effective. Another key result of the dose ranging experimentation is that G-HSA-B with an average of only 1 biotin per molecule is presumably only clearing the MAb-StrAv conjugate via the Ashwell receptor mechanism only, because too few biotins are present to cause cross-linking and aggregation of MAb-StrAv conjugates and clearing agents with such aggregates being cleared by the reticuloendothelial system.

D. Tumor Targeting Evaluation Using G-HSA-B.

The protocol for this experiment was as follows:
Time 0: administer 400 micrograms MAb-StrAv conjugate;
Time 24 hours: administer 240 micrograms of G-HSA-B with one biotin and 12–45 galactoses and Time 26 hours: administer 6 micrograms of

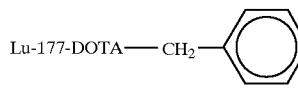 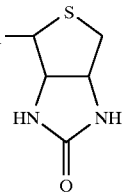

Lu-177 is complexed with the DOTA chelate using known techniques therefor.

Efficient delivery of the Lu-177-DOTA-biotin small molecule was observed, 20–25% injected dose/gram of tumor. These values are equivalent with the efficiency of the delivery of the MAb-StrAv conjugate. The AUC tumor/AUC blood obtained for this non-optimized clearing agent dose was 300% greater than that achievable by comparable direct MAb-radiolabel administration. Subsequent experimentation has resulted in AUC tumor/AUC blood over 1000% greater than that achievable by comparable conventional MAb-radiolabel administration. In addition, the HSA-based clearing agent is expected to exhibit a low degree of immunogenicity in humans.

EXAMPLE V

Small Molecule Clearing Agent Preparation

Figure 2A:
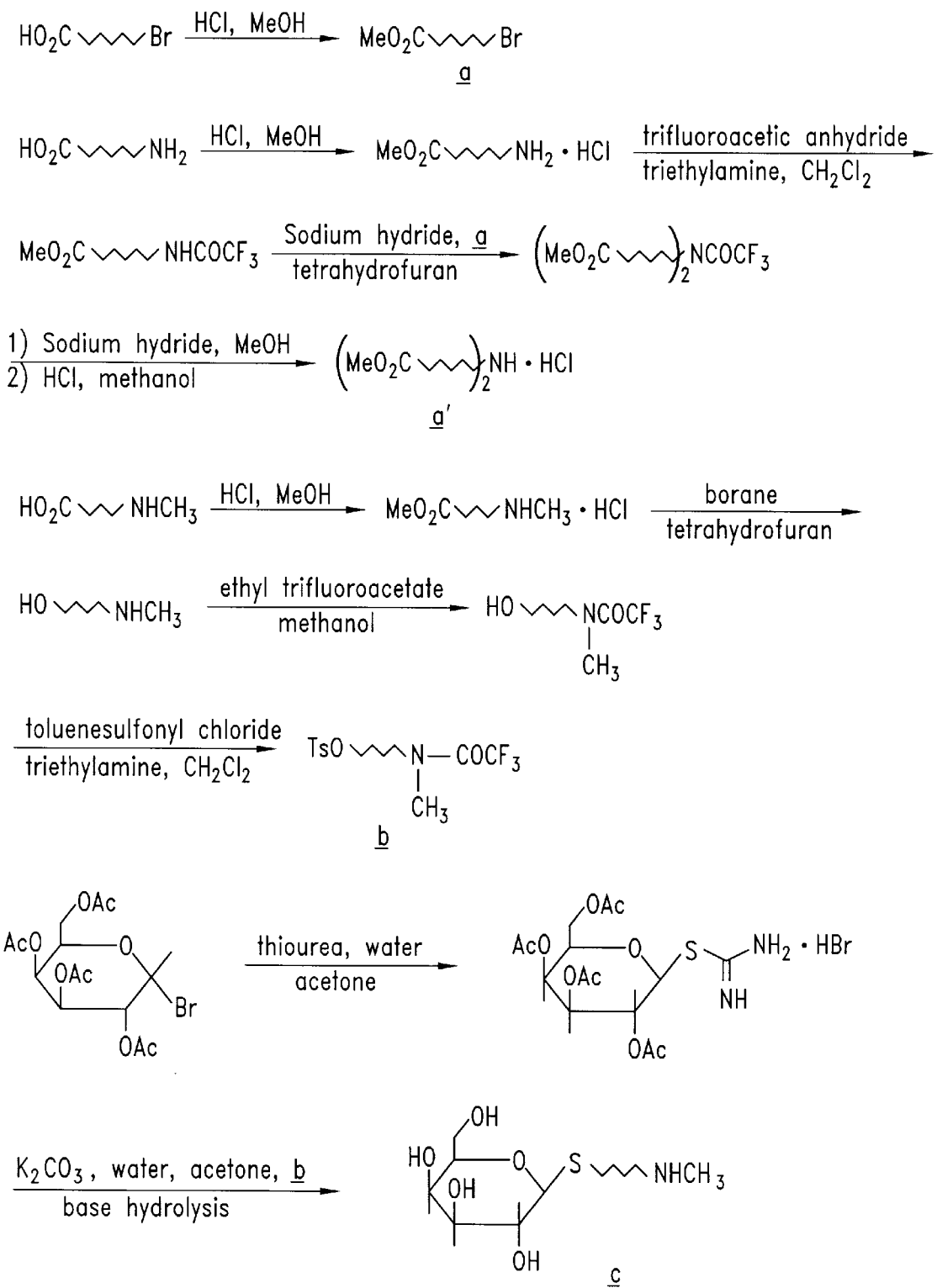
FIGS. 2a, 2b and 2c schematically depict the preparation of a sixteen galactose cluster-biotin conjugate.
Figure 2B:
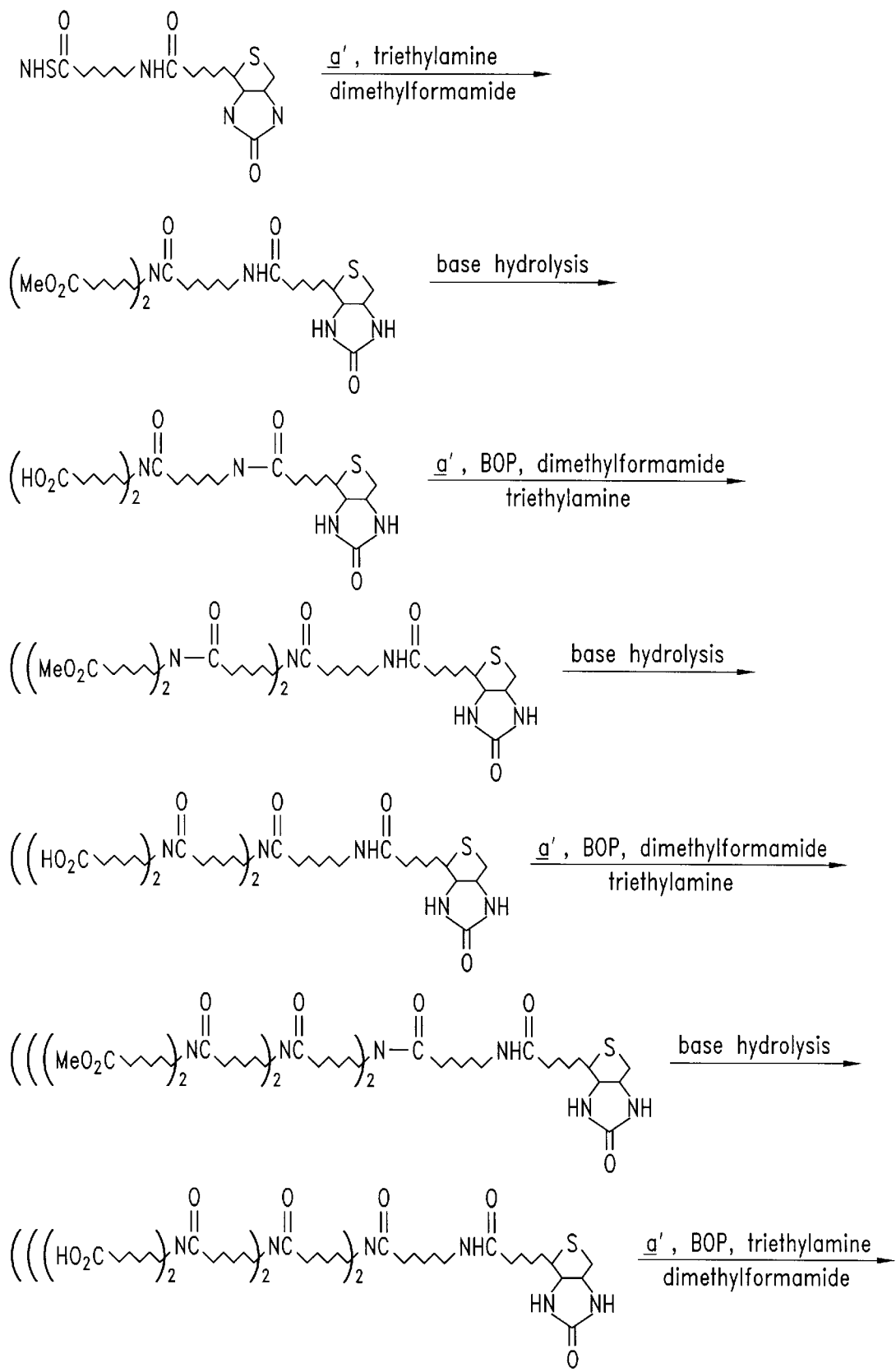
Figure 2C:
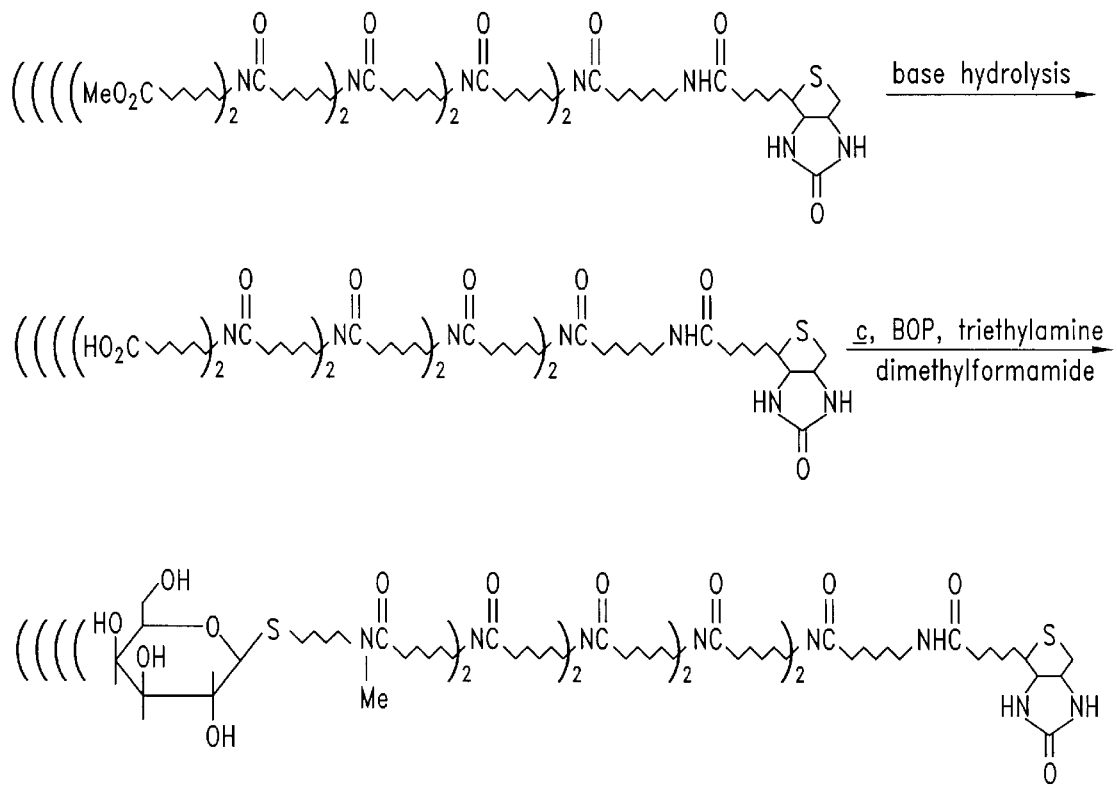

This procedure is shown schematically in FIG. 2.

Methyl 6-bromohexanoate. To a 1 L round bottom flask, charged with 20 g (102.5 mmol) of 6-bromohexanoic acid and 500 mL of methanol, was bubbled hydrogen chloride gas for 2–3 minutes. The mixture was stirred at room temperature for 4 hours and concentrated to afford 21.0 g of the product as a yellow oil (99%): $^1$H-NMR (200MHz, $d_6$-DMSO); 3.57 (s, 3H), 3.51 (t, 2H), 2.30 (t, 2H), 1.78 (pentet, 2H), and 1.62–1.27 (m, 4H) ppm.

Methyl 6-aminohexanoate hydrochloride. To a 1 L round bottom flask, charged with 40.0 g aminocaproic acid, was added 500 mL of methanol. Hydrogen chloride gas was bubbled through the mixture for 5 minutes, and the mixture was stirred at room temperature for 5 hours. The mixture was then concentrated via rotary evaporation and then under full vacuum pump pressure (<0.1 mm Hg) to afford 55 g of the product as a white solid (99%): $^1$H-NMR (200 MHz, $CD_3OD$); 3.67 (s, 3H), 3.02 (t, 2H), 2.68 (s, 3H), 2.48 (t, 2H), and 2.03–1.87 (pentet, 2H) ppm.

Methyl 6-(trifluoroacetamido)-hexanoate: To a 1 L round bottom flask, charged with 25.0 g (138 mmol) of methyl 6-aminohexanoate hydrochloride and 500 mL of methylene chloride, was added 24 mL (170 mmol) trifluoroacetic anhydride. The mixture was cooled in an ice bath, and 42 mL (301 mmol) of triethylamine was added over a 25–30 minute period. The mixture was stirred at 0° C. to room temperature for 2 hours and then concentrated. The residue was diluted with 150 mL of diethyl ether and 150 mL of petroleum ether, and the resulting solution was washed first with 1N aqueous HCl (3×150 mL) and then with saturated aqueous sodium bicarbonate (3×150 mL). The organic phase was dried over magnesium sulfate, filtered and concentrated to give 32.9 g of the product as a pale yellow oil (99%): $^1$H-NMR (200MHz, $d_6$-DMSO); 9.39 (m, 1H), 3.57 (s, 3H), 3.14 (q, 2H), 2.29 (t, 2H), 1.60–1.38 (m, 4H), and 1.32–1.19 (m, 2H) ppm.

N,N'-Bis(6-methoxycarbonylhexvl)amine hydrochloride. To a 500 mL dry round bottom flask, charged with 12.0 g (50.0 mmol) of the secondary amide, methyl 6-(trifluoroacetamido)-hexanoate, and 250 mL of dry tetrahydrofuran, was added 2.2 g (55 mmol, 1.1 equiv) of 60% sodium hydride. The mixture was stirred at room temperature for 30 minutes and then 10.25 g (49.0 mmol, 0.98 equiv) of the alkyl bromide, methyl 6-bromohexanoate, was added. The mixture was stirred at reflux for 3 hours. an additional 5.80 g (27.7 mmol, 0.55 equiv) of methyl 6-bromohexanoate was added, and the mixture was stirred at reflux for 70 hours. The mixture was cooled, diluted with 150 mL of 1N aqueous HCl and then extracted with ethyl acetate (3×100 mL). The organic extracts were combined, dried over magnesium sulfate, filtered and concentrated. The residue was diluted with 200 mL of methanol and then treated with 30 mL of 10N aqueous sodium hydroxide. The mixture was stirred at room temperature for 18 hours and then concentrated. The residue was diluted with 200 mL of deionized water and acidified to pH 1–2 with 37% concentrated HCl. The solution was washed with diethyl ether (3×100 mL). The aqueous phase was concentrated. The residue was diluted with 200 mL of methanol and reconcentrated. The subsequent residue was diluted with 250 mL of methanol, and HCl gas was bubbled through for 2–3 minutes followed by stirring at room temperature for 3 hours. The mixture was concentrated. The residue was diluted with 300 mL of methanol and filtered to remove inorganic salts. The filtrate was treated with 3 g of activated charcoal, filtered through Celite (manufactured by J. T. Baker) and concentrated. The residue, an off-white solid, was recrystallized from 100 mL of 2-propanol to afford 7.0 g of the product as a white solid. Concentration of the filtrate and further recrystallization of the residue yielded an additional 1.65 g of the product for a total of 8.65 g (56%) $^1$H-NMR (200 MHz, $d_6$-DMSO); 3.57 (s, 3H), 2.90–2.73 (m, 4H), 2.30 (t, 4H), 1.67–1.44 (m, 8H), and 1.37–1.20 (m, 4H) ppm.

Methyl 4-methylaminobutyrate hydrochloride. To a 1 L round bottom flask, charged with 30.0 g (195 mmol) of 4-methylaminobutyric acid and 500 mL of methanol, was bubbled HCl gas for 1–2 minutes. The mixture was stirred at room temperature for 3–4 hours and then concentrated to afford 32.5 g of the product as a foamy, off-white solid (99%): $^1$H-NMR (200 MHz, $CD_3OD$); 3.67 (s, 3H), 3.03 (t, 2H), 2.68 (s, 3H), 2.48 (t, 2H), and 2.03–1.87 (pentet, 2H) ppm.

4-Methylaminobutanol. To a 1 L round bottom flask, charged with 32.5 g (194 mmol) of the ester, methyl 4-methylaminobutyrate hydrochloride, was added 500 mL of 1M borane in tetrahydrofuran over a 1 hour period at 0° C. After the addition was complete, the mixture was refluxed for 20 hours, cooled to 0° C., and the excess borane was destroyed by careful addition of 100 mL of methanol. After all the methanol was added, the mixture was stirred at room temperature for 1 hour and then concentrated. The residue was diluted with 400 mL of methanol and then HCl gas was bubbled into the solution for 5 minutes. The mixture was refluxed for 16 hours. The mixture was cooled, concentrated and then diluted with 250 mL of deionized water. The product was initially free based by addition of 10N aqueous sodium hydroxide, to a pH of 9–9.5, and then by addition of 70 g of AG 1 X-8 anion exchange resin (hydroxide form commercially available from BioRad), and by stirring the solution for 2 hours. The resin was filtered off and washed with 150 mL of deionized water. The aqueous filtrates were combined and concentrated. The residue was diluted with 200 mL of 2-propanol and filtered. The collected solids were rinsed with 100 mL of 2-propanol. The organic filtrates were combined and concentrated. The residue was distilled under reduced pressure to afford 12.85 g of the product as a colorless oil (bp 68° C. at 0.1–0.2 mm HG; 64%): $^1$H-NMR (200 MHz, $D_2O$); 3.52 (t, 2H), 2.56 (t, 2H), 2.31 (s, 3H), and 1.65–1.43 (m, 4H) ppm.

4-(N-Methyl-trifluoroacetamido)-1-butanol. To a 250 mL round bottom flask, charged with 10.0 g (96.9 mmol) of the amine, 4-methylaminobutanol, in 100 mL of dry methanol, was added 17.5 mL (147 mmol) of ethyl trifluoroacetate. The mixture was stirred at room temperature for 24 hours and then concentrated to afford 18.55 g of the product as a near colorless oil (96%): $^1$H-NMR (200 MHz, $D_2O$); 3.63 and 3.50 (2t's, 4H), 3.20 and 3.05 (d and s, 3H), and 1.82–1.47 (m, 4H) ppm.

1-(P-Toluenesulfonyloxv)-4-(N-methyl-trifluoroacetamido)butane. To a 1 L dry round bottom, flask, charged with 17.0 g (85.4 mmol) of the alcohol, 4-(N-methyl-trifluoroacetamido-l-butanol, in 400 mL of methylene chloride, was added 17.1 g (89.7 mmol, 1.05 equiv) of toluenesulfonyl chloride followed by 30 mL (213 mmol, 2.5 equiv) of triethylamine at 0° C. over a 10 minute period. The mixture was stirred at 0° C. to room temperature for 15 hours and then washed with 5% v/v aqueous HCl (3×200 mL). The organic phase was dried over magnesium sulfate, filtered and concentrated. The residue was chromatographed on silica gel, eluting with 50:50 hexane/methylene chloride and then with methylene chloride, to give. 25.1 g of the product as a pale yellow oil (83%): $^1$H-NMR (200 MHz, $CDCL_3$); 7.80 (d, 2H), 7.37 (d, 2H), 4.07 (m, 2H), 3.41 (m, 3H), 3.09 and 2.98 (q and s, 3H), 2.45 (s, 3H), and 1.68 (m, 4H) ppm: TLC (methylene chloride) $R_f$=0.31.

1-S-(2,3,4,6-tetra-O-acetyl-beta-D-galacto-pyranosyl)-2-thiopseudourea hydrobromide. To a 250 mL round bottom flask, charged with 5.08 g (60.8 mmol, 1.09 equiv) of.thiourea and 36 mL of acetone, was added 25.0 g. (66.7 mmo9l) of tetra-acetyl-alpha-D-galactopyranosyl bromide. The mixture was stirred at reflux for 15–20 minutes and then cooled on ice. The mixture was filtered into a Buchner funnel and rinsed with 25 mL of ice cold acetone. The solids were treated with 50 mL of acetone, refluxed for 15 minutes, cooled on ice, and filtered. The solids were rinsed with 25 mL of cold acetone, air dried and then dried under vacuum to give 22.6 g of the product as a white solid (76%): $^1$H-NMR (200MHz, $d_6$-DMSO); 9.4–9.0 (broad d, 4H), 5.63 (d, 1H), 5.38 (d, 1H), 5.23 (dd, 1H), 5.09 (t, 1H), 4.40 (t, 1H), 4.04 (dd, 1H), 2.13 (s, 3H), 2.08 (s, 3H), 2.00 (s, 3H), 1.93 (s, 3H) ppm.

4-(N-Methylaminobutyl)-1-thio-beta-D-galactoovranoside. To a 500 mL round bottom flask, charged with 20.7 g (42.5 mmol, 1.07 equiv) of the thiopseudourea hydrobromide prepared as described above in 70 mL of deionized water, was added 6.4 g (46.3 mmol, 1.16 equiv) of potassium carbonate and 4.7 g (45.2 mmol, 1.13 equiv) of sodium bisulfite followed immediately by 14.1 g (39.9 mmol, 1.0 eguiv) of the tosylate, 1-(p-toluenesulfonyloxy)-4-(N-methyltrifluoroacetamido)butane in 70 mL of acetone. The mixture was stirred at room-temperature for 16 hours. The mixture was diluted with 50 mL of brine and extracted with ethyl acetate (3×200 mL). The organic extracts were combined, dried over magnesium sulfate, filtered and.concentrated. The residue was chromatographed on silica gel, eluting first with 75% methylene chloride/hexane, followed by methylene chloride, then with 2% methanol/methylene chloride and finally with 10% methanol/methylene chloride. Fractions containing alkylation product with different degrees of acetylation were combined and concentrated. The residue was diluted with 250 mL of methanol and 150 mL of deionized water.and treated with 110 g of AG-1 X-8 resin (hydroxide form; 2.6 m equivig dry weight) commercially available from BioRad. The mixture was stirred at room temperature for 18 hours. The mixture was filtered, and the resin was rinsed with methanol (2×150 mL). The filtrates were combined and concentrated to afford 6.1 g of product (54%): $^1$H-NMR (200 MHz, $D_2O$); 4.38 (d, 1H), 3.88 (d, 1H), 3.69–3.41 (m, 5H), 2.82–2.64 (m, 4H), 2.43 (s, 3H), and 1.68–1.57 (, 4H) ppm.

Biotin bis-methyl ester: To a 50 mL round bottom flask, charged with 1.00 g (3.23 mmol, 1.13 equiv) of amine hydrochloride, N,N'-bis-(6-methoxycarbonyl-hexyl)amine hydrochloride), and 1.30 g (2.86 mmol) of caproamidobiotin-NHS-ester (preparable by standard methods or commercially available from Sigma Chemical Company) and 10 mL of dry dimethylformamide, was added 1.5 mL (10.6 mmol) of triethylamine. The mixture was stirred at 85° C. for 2 hours and then concentrated via reduced pressure rotary evaporation. The residue was chromatographed on silica gel, eluting with 75:25:0.05 ethyl acetate/methanol/acetic acid, to afford 1.63 g of the product as a white foamy solid (93%): $^1$H-NMR (200 MHz $d_6$-DMSO); 7.72 (t, 1H), 6.41 (s, 1H), 6.34 (s, 1H), 4.29 (m, 1H), 4.11 (m, 1H), 3.57 (s, 6H), 3.23–2.91 (m, 7H) 2.81 (dd, 1H), 2.55 (d, 1H), 2.35–2.13 (m, 6H), 2.03 (t, 2H), 1.65–1.10 (m, 24H) ppm: TLC; $R_f$=0.58 (75:25:0.01 ethyl acetate/methanol/acetic acid).

Biotin bis-acid: To a 200 mL round bottom flask, charged with 1.61 g (2.63 mmol) of biotin bis-methyl ester and 50 mL of methanol, was added 5 mL of 3N aqueous sodium hydroxide. The mixture was stirred at 40° C. for 3 hours and then concentrated via reduced pressure rotary evaporation. The residue was diluted with 50 mL of deionized water, and then 3N aqueous HCl was added until a pH of 1–2 was attained. The mixture was again concentrated. The residue was chromatographed on C-18 reverse phase silica gel, eluting first with 20:80:–0.1 acetonitrile/water/trifluoroacetic acid and then with 50:50:0.1 acetonitrile/water/trifluoroacetic acid. The fractions containing product were combined and concentrated. The residue was diluted with 40 mL of water and 20 mL of acetonitrile. The solution was frozen (–70° C.) and lyophilized to afford 1.42 g of the product as a fluffy white solid (92%): $^1$H-NMR (200 MHz $d_6$-DMSO); 7.72 (t, 1H), 6.61 (broad s, 2H), 4.29 (m, 1H), 4.11 (m, 1H), 3.35–2.93 (m, 7H) 2.81 (dd, 1H), 2.55 (d, 1H), 2.28–2.12 (m, 6H), 2.03 (t, 2H), 1.68–1.10 (m, 24H) ppm: TLC; $R_f$=0.30 (50:50:0.01 acetonitrile/water/trifluoroacetic acid).

Biotin tetra-methyl ester: To a 50 mL round bottom flask, charged with 350 mg (0.599 mmol) of the biotin bis-acid, 402 mg (1.30 mmol, 2.16 equiv) of amine hydrochloride, N,N'-bis-((6-methoxycarbonyl-hexyl)amine hydrochloride), and 10 mL of dry dimethylformamide, was added 556 mg (1.26 mmol, 2.10 equiv) BOP and 500 microliters (3.54 mmol, 5.91 equiv) of triethylamine. The mixture was stirred at room temperature for 2 hours and then concentrated via reduced pressure rotary evaporation. The residue was chromatographed on C-18 reverse phase silica gel, eluting first with 50:50 methanol/water and then with 85:15 methanol/water, to afford 618 mg of the product as a foamy white solid (95%): $^1$H-NMR (200 MHz d$_6$-DMSO); 7.71 (t, 1H), 6.1 (broad s, 2H), 4.29 (m, 1H), 4.11 (m, 1H), 3.57 (s, 12H), 3.25–2.91 (m, 15H) 2.81 (dd, 1H), 2.55 (d, 1H), 2.35–2.12 (m, 14H), 2.02 (t, 2H), 1.65–1.10 (m, 48H) ppm: TLC; R$_f$=0.48 (85:15 methanol/water).

Biotin tetra-acid: To a 50 mL round bottom flask, charged with 350 mg (0.319 mmol) of biotin tetramethyl ester and 15 mL of methanol, was added 5 mL of 1N aqueous sodium hydroxide and 5 mL of deionized water. The mixture was stirred at room temperature for 14 hours and then concentrated via reduced pressure rotary evaporation. The residue was diluted with 15 mL of deionized water, acidified to pH 1–2 by addition of 6N aqueous HCl and then reconcentrated. The residue was chromatographed on C-18 reverse phase silica gel, eluting first with 50:50 methanol/water and then with 70:30 methanol/water. The fractions containing the product were combined and concentrated. The residue was diluted with 10 mL of water and 8 mL of acetonitrile. The solution was frozen (–70° C.) and lyophilized to afford 262 mg of the product as a fluffy white solid (79%): $^1$H-NMR (200 MHz d$_6$-DMSO); 7.71 (t, 1H), 6.41 (s, 1H), 6.34 (s, 1H), 4.29 (m, 1H), 4.11 (m, 1H), 3.25–2.93 (m, 15H) 2.81 (dd, 1H), 2.55 (d, 1H), 2.31–2.10 (m, 14H), 2.02 (t, 2H), 1.63–1.09 (m, 48H) ppm: TLC; R$_f$=0.45 (70:30 methanol/water).

Biotin octa-methyl ester: To a 25 mL round bottom flask, charged with 220 mg (0.710 mmol, 4.93 equiv) of amine hydrochloride, N,N'-bis-(6-methoxycarbonyl-hexyl)amine hydrochloride), 150 mg (0.144 mmol) of the biotin tetra-acid, and 5 mL of dry dimethylformamide, was added 300 mg (0.678 mmol, 4.71 equiv) BOP followed by 500, microliters (3.54 mmol, 24.0 equiv) of triethylamine. The mixture was stirred at room temperature for 3 hours and then concentrated via reduced pressure rotary evaporation. The residue was chromatographed on C-18 reverse phase silica gel, eluting first with 60:40 methanol/water and then with 90:10 methanol/water, to afford 246 mg of the product as a foamy white solid (83%): $^1$H-NMR (200 MHz d$_6$-DMSO) ;-7.71 (t, 1H), 6.41 (s, 1H), 6.34 (s, 1H), 4.29 (m, 1H), 4.11 (m, 1H), 3.57 (s, 24H), 3.25–2.91 (m, 31H) 2.81 (dd, 1H), 2.55 (d, 1H), 2.32–2.12 (m, 30H), 2.02 (t, 2H), 1.65–1.08 (m, 96H) ppm: TLC; R$_f$=0.42 (90:10 methanol/water).

Biotin octa-acid: To a 50 mL round bottom flask, charged with 235 mg (0.114 mmol) of biotin octa-methyl ester and 10 mL of methanol, was added 5 mL of 1N aqueous sodium hydroxide and 5 mL of deionized water. The mixture was stirred at room temperature for 14 hours and then concentrated via reduced pressure rotary evaporation. The residue was diluted with 10 mL of deionized water, acidified to pH 1–2 by addition of 6N aqueous HCl and then reconcentrated. The residue was chromatographed on C-18 reverse phase silica gel, eluting first with 50:50 methanol/water and then with 75:25 methanol/water. The fractions containing the product were combined and concentrated. The residue was diluted with 20 mL of 1:1 (ratio by volume) acetonitrile/water. The solution was frozen (–70° C.) and lyophilized to afford 202 mg of the product as a fluffy white solid (91%): 1H-NMR (200 MHz d$_6$-DMSO); 7.71 (t, 1H), 6.41 (s, 1H), 6.34 (s, 1H), 4.29 (m, 1H), 4.11 (m, 1H), 3.29–2.91 (m, 31H) 2.81 (dd, 1H), 2.55 (d, 1H), 2.31–2.10 (m, 30H), 2.03 (t, 2H), 1.65–1.09 (m, 96H) ppm: TLC; R$_f$=0.51 (75:25 methanol/water).

Biotin hexadeca-methyl ester: To a 25 mL round bottom flask, charged with 154 mg (0.497 mmol, 10.0 equiv) of amine hydrochloride, N,N'-bis-(6methoxycarbonyl-hexyl) amine hydrochloride), 97 mg (0.0497 mmol) of the biotin octa-acid, and 5 mL of dry dimethylformamide, was added 202 mgr (0.457 mmol, 9.2 equiv) BOP followed by 500 microliters (3.54 mmol, 71.2 equiv) of triethylamine. The mixture was stirred at room temperature for 8 hours and then concentrated via reduced pressure rotary evaporation. The residue was chromatographed on silica gel, eluting first with 70:30 methanol/water and then with 95:5 methanol/water; to afford 149 mg of the product as a foamy white solid (75%): $^1$H-NMR (200 MHz d$_6$-DMSO); 7.71 (t, 1H), 6.41 (s, 1H), 6.34 (s, 1H), 4.29 (m, 1H), 4.11 (m, 1H), 3.57 (s, 48H), 3.25–2.92 (m, 63H) 2.81 (dd, 1H), 2.55 (d, 1H), 2.35–2.11 (m, 62H), 2.01 (t, 2H), 1.65–1.08 (m, 192H) ppm: TLC; R$_f$=0.31 (95:5 methanol/water).

Biotin hexadecyl-acid: To a 50 mL round bottom flask, charged with 141 mg (0.0353 mmol) of biotin hexadeca-methyl ester and 15 mL of methanol, was added 8 mL of IN aqueous sodium hydroxide and 5 mL of deionized water. The mixture was stirred at room temperature for 14 hours and then concentrated via reduced pressure rotary evaporation. The residue was diluted with 15 mL of deionized water, acidified to pH 1–2 by addition of 6N aqueous HCl and then reconcentrated. The residue was chromatographed on C-18 reverse phase silica gel, eluting first with 60:40 methanol/water and then with 85:15 methanol/water. The fractions containing the product were combined and concentrated. The residue was diluted with 20 mL of 1:1 acetonitrile/water. The solution was frozen (–70° C.) and lyophilized to afford 130 mg of the product as a fluffy white solid (75%): H-NMR (200 MHz d$_6$-DMSO); 7.71 (t, 1H), 6.41 (s, 1H), 6.34 (s, 1H), 4.29 (m, 1H), 4.11 (m, 1H), 3.26–2.92 (m, 63H) 2.81 (dd, 1H), 2.55 (d, 1H), 2.35–2.10 (m, 62H), 2.01 (t, 2H), 1.65–1.09 (m, 192H) ppm: TLC; R$_f$=0.64 (85:15 methanol/water).

Hexadeca-galactosyl biotin:. To a 25 mL round bottom flask, charged with 125 mg (0.0332 mmol) of biotin hexadeca-acid, 179 mg (0.636 mmol, 19.2 equiv) of galactose-amine, 4-(N-methylaminobutyl)-1-thio-beta-D-galactopyranoside, and 4 mL of dry methylformamide, was added 264 mg (0.597 mmol, 18.0 equiv) of BOP followed by 400 microliters (2.87 mmol, 86.5 equiv) of dry triethylamine. The mixture was stirred at room temperature for 17 hours and then concentrated via reduced pressure rotary evaporation. The residue was chromatographed on C-18 reverse phase silica gel, eluting first with 60:40 methanol/water and then with 75:25 methanol/water. The fractions containing the product were combined and concentrated and rechromatographed on C-18 reverse phase silica. gel, eluting first with 40:60:0.1 acetonitrile/water/trifluoroacetic acid and then with 50:50:0.1 acetonitrile/water/trifluoroacetic acid. The fractions containing the product were again combined and concentrated. The residue was dissolved in 20 mL of water. The solution was frozen (−70° C.) and lyophilized to afford 173 mg of the product as a fluffy white solid (75%): $^1$H-NMR (200 MHz D$_2$O); 4.52 (m, 1H), 4.37 (d, 15H), 3.90 (d, 16H), 3.70–3.42 (m, 80H), 3.41–3.05 (m, 97H), 2.98–2.82 (2s and 2m, 49H), 2.80–2.49 (m, 33H), 2.44–2.11 (m, 62H), 1.75–1.10 (m, 256H) ppm: TLC; R$_f$=0.53 (75:25 methanol /water).

The above procedure is designed for the formation of a galactose cluster of 16 galactose residues. The four or eight galactose versions can be made in accordance with this procedure by proceeding from the tetra acid or the octa acid to the galactose derivatization step, which was described above for the 9 16-galactose cluster. Similarly, 32, etc. galactose cluster constructs can be prepared in accordance with the present invention by introduction of more iterations of the methyl ester and acid formation steps. When the desired number of acid residues are formed, the galactose derivatization step is employed, with the proportions of the components adjusted to accommodate the number of acid residues.

EXAMPLE VI

Small Molecule Clearing Agent Evaluation

In order to demonstrate the efficacy of the described small molecule clearing agents, a number of such conjugates were synthesized using a biotin binding moiety and galactose residue cluster directors. These conjugates were synthesized using different numbers of attached galactose residues. In addition, these conjugates contained either the long chain linker (LC=containing an aminocaproyl spacer between the amine associated with galactose and the carboxyl moiety associated with the biotin) or the short chain linker (SC= direct link between the amine associated with galactose and the carboxyl moiety associated with the biotin) as set forth below.

The conjugates involved in the testing are depicted below:

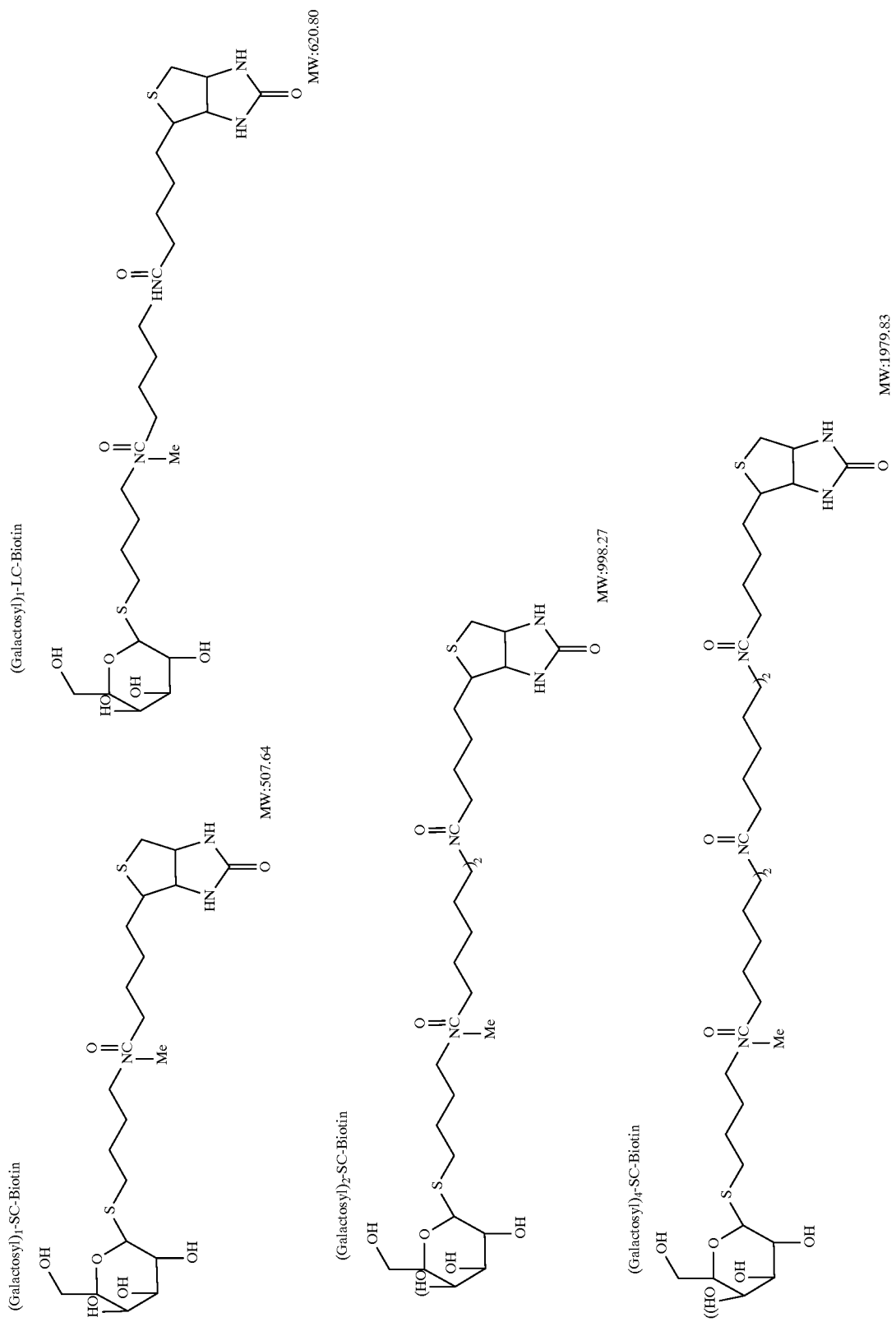

-continued
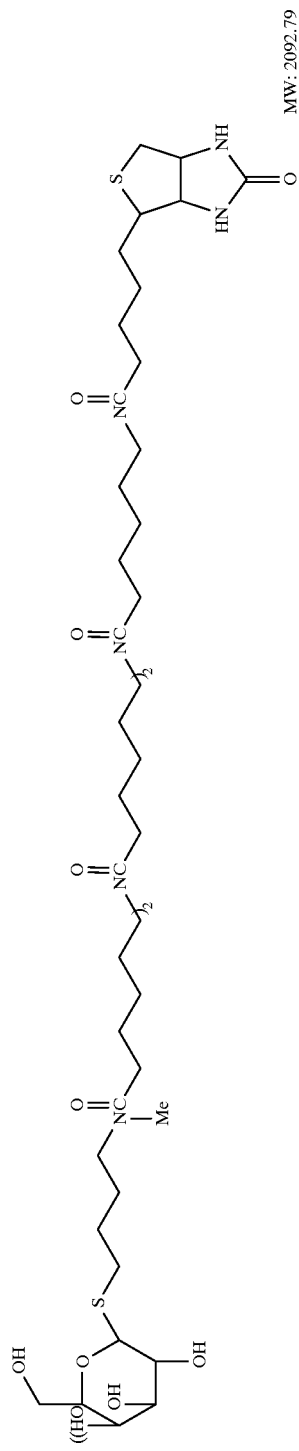
(Galactosyl)₄-LC-Biotin  MW: 2092.79
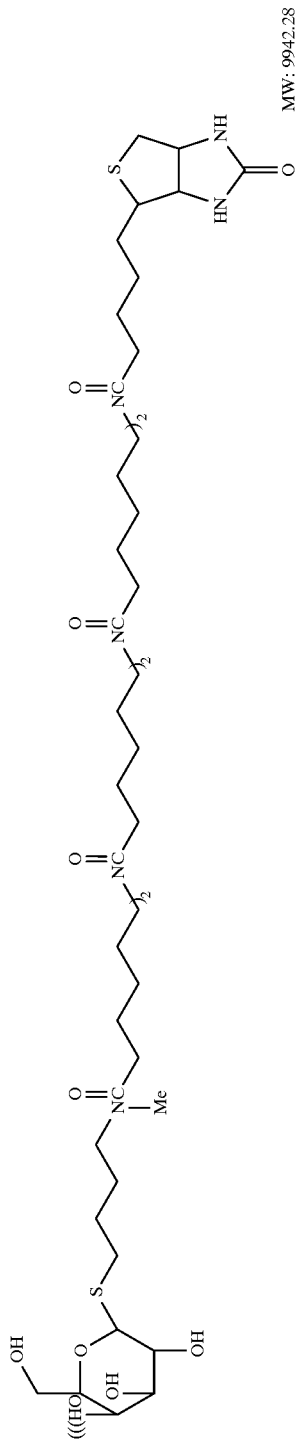
(Galactosyl)₈-SC-Biotin  MW: 9942.28
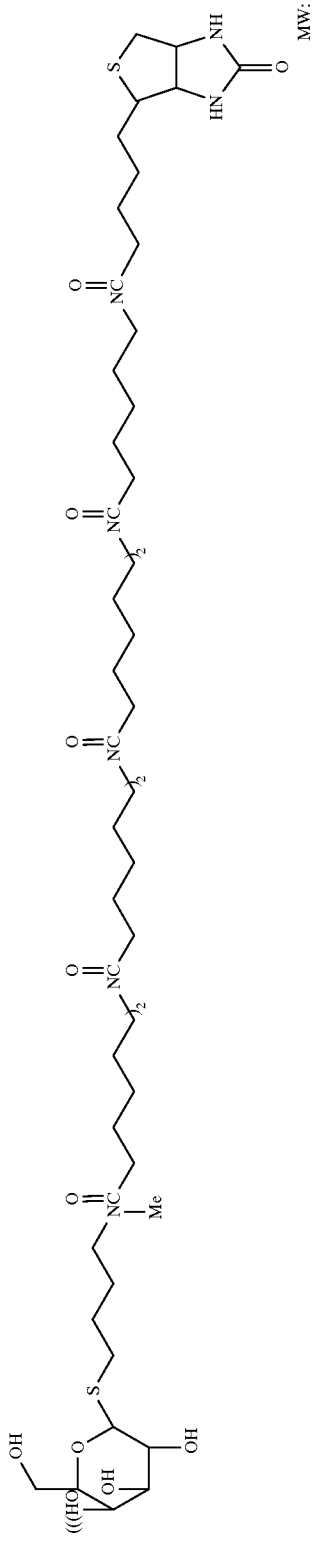
(Galactosyl)₉-LC-Biotin  MW: 4066.42

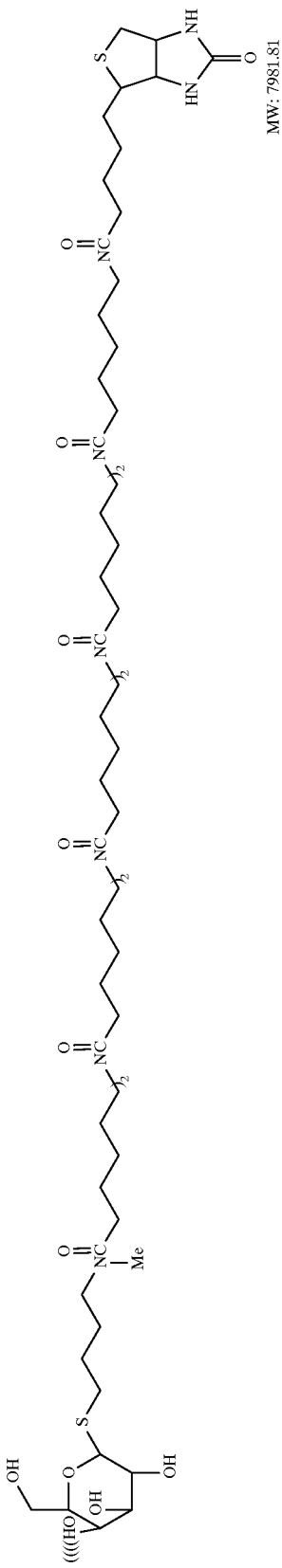

Some or all of these compounds were assayed for their clearance directing activity in two sets of experiments. The first set of experiments involved ex vivo preparation of a precomplexed monoclonal antibody-streptavidin-biotin-galactose cluster conjugate labeled with I-125, intravenous administration of the conjugate in a mouse model, and measuring serum levels of the conjugate over time. The second set of experiments involved intravenous administration of MAb-streptavidin conjugate followed by administration of biotin-galactose cluster conjugate.

NR-LU-10 antibody (MW 150 kD) was conjugated to streptavidin (MW 66 kD) (as described in Example II above), and radiolabeled with $^{125}$I/PIP-NHS as described below. The antibody component of the conjugate was radioiodinated using p-aryltin phenylate NHS ester (PIP-NHS) and $^{125}$I sodium iodide. In general, the experimentation involving the 2, 4 and 8 galactose-biotin constructs was conducted in an analogous manner to that for the 16 galactose-biotin construct as described below.

The data from these experiments indicates that no significant increase in serum clearance (in comparison to the MAb-Streptavidin conjugate itself) occurs until at least 4 galactose residues are attached to the biotin molecule. In addition, the data indicates that the longer linker separating the galactose cluster from the biotin molecule resulted in better clearance rates. This is consistent with the inventors' belief that the galactose cluster interferes with binding to the conjugate to be cleared if an appropriate length spacer is not used to minimize steric interactions or that sugar-hepatocyte interaction is sterically precluded.

In a third set of experiments conducted in vivo in the pretargeting format (e.g., administration of radiolabeled MAb-streptavidin conjugate followed by administration of clearing agent), the (galactosyl)$_8$-LC-biotin conjugate was also compared to galactose-HSA-biotin prepared as described above. This comparison was conducted in a Balb/c mouse model and was for the ability to clear an I-125 labeled monoclonal antibody-streptavidin conjugate (1–125 LU-10-streptavidin) from circulation as a function of time. The results of this experiment indicate that the (galactosyl)$_8$-LC-biotin conjugate is comparable to galactosylated-HSA-biotin in its ability to clear the streptavidin-containing conjugate from circulation. Subsequent experiments have further shown that hepatic-directed compounds containing 16 galactose residues provide for even better clearance than those containing 8 galactose residues.

Experiments were designed and executed to evaluate a 16 galactose cluster-biotin construct without the stabilizing tertiary amine structure of the nitrogen of the amide closest to the biotin, the preparation of such a stabilized construct being described above in Example V. BALB/c female mice (20–25 g) were injected i.v. with 120 micrograms of NR-LU-10-streptavidin conjugate radiolabeled with I-125, and blood was serially collected from n=3 mice. The clearance of the conjugate from the blood was measured of these control mice. Separate groups of mice were injected with either 120 or 12 micrograms of radiolabeled monoclonal antibody-streptavidin conjugate which had been precomplexed with the 16 galactose-biotin construct by mixing the biotin analog at a 20-fold molar excess with the antibody conjugate, and purifying the excess small molecule from the protein by size exclusion chromatography. Both doses of precomplexed conjugate showed extremely rapid clearance from the blood, relative to the antibody conjugate control.

Having shown that precomplexed material could clear rapidly and efficiently from the blood, experiments were conducted to measure the effectiveness of various doses of the 16 galactose-biotin construct to form rapidly clearing complexes in vivo. Mice received 400 micrograms of I-125 NR-LU-10streptavidin conjugate intravenously, and approximately 22 hours later received the 16 galactose-biotin construct at doses of 100 50, or 10:1 (456, 228 and 45 micrograms, respectively) molar excess to circulating monoclonal antibody-streptavidin conjugate. While each dose was effective at clearing conjugate, the most effective dose (both kinetic and absolute) was the 10:1 dose. For the larger doses, there appears to be some saturation of the liver receptor, since both larger doses show a plateau in conjugate clearance for about 1 hour after administration of the 16 galactose-biotin construct. The larger doses may be sufficiently high to achieve competition between complexed and non-complexed 16-galactose-biotin for liver receptors, thereby precluding all but a small initial fraction of the complexed MAb-streptavidin conjugate from clearing via the liver. Following the plateau period, clearing of the conjugate remained slow and was eventually less complete than that achieve with the lower dose (approximately 10% of the conjugate remained in circulation at the higher doses, in comparison to 2% for the lower dose). An alternative explanation for this finding rests on the fact that the 16-galactose-biotin construct was not stabilized to potential biotinidase-mediated cleavage (e.g., the chemical synthesis did not incorporate a methyl, lower alkyl, carboxylic acid, lower alkyl carboxylic acid or like group was not bound to the amide nitrogen most closely adjacent the biotin rather than hydrogen). If the 16 galactose-biotin construct is unstable, sufficient biotin may be released at higher doses to that a significant portion of circulating conjugate became blocked thereby and, consequently, was not cleared via hepatic-mediated uptake.

Evident in all groups is the lack of a "rebound" or gradual increase in blood levels of circulating conjugate following disruption of the equilibrium between vascular and extravascular concentrations of conjugate. This constitutes the best evidence to date that galactose cluster-biotin constructs extravasate into extravascular fluid, and that conjugate which is. complexed extravascularly clears very rapidly when it passes back into the vascular compartment.

Further experimentation in the same animal model compared (galactose)$_{35}$-HSA-(biotin)$_2$ clearing agents prepared as described above and decreasing doses of 16 galactose-biotin construct as in vivo clearing agents. A 46 microgram dose of 16 galactose-biotin was found to be optimal and more effective than the previously optimized dose of (galactose)$_{35}$-HSA-(biotin)$_2$. Lower (12 and 23 microgram) and higher (228 microgram) doses of 16 galactose-biotin were less efficient at removing circulating conjugate, and the lower doses showed a significant rebound effect, indicating that incomplete complexation with circulating conjugate may have occurred.

Having shown that effective clearing could be achieved with the appropriate does of 16 galactose-biotin construct, studies were undertaken in tumored nude mice to evaluate the potential blockade of tumor-associated conjugate by the small 16 galactose-biotin. Mice bearing either SW-1222 colon tumor xenografts or SHT-1 small cell lung cancer (SCLC) tumor xenografts were pretargeted with NR-LU-10-streptavidin conjugate and, 22 hours later, received 46 micrograms of 16 galactose-biotin. After 2 hours, Y-90-DOTA-biotin prepared as described above was administered, and its uptake and retention in tumor and non-target tissues was evaluated by sacrifice and tissue counting for radioactivity 2 hours post-administration.

In comparison to historical controls employing (galactose)$_{35}$-HSA-(biotin)$_2$, tumor targeting was slightly lower in the high antigen-expressing colon xenograft and was slightly higher in the low antigen-expressing SCLC xenograft. Given the normal variability in such experiments, tumor uptake of radioactivity was assessed as roughly equivalent, a surprising result given the potential for target uptake of 16 galactose-biotin. Non-target organ uptake was comparable in all tissues except liver, where animals receiving 16 galactose-biotin showed slightly higher levels. The historical controls were conducted with a 3 hour time period between clearing agent and radioactivity administration. When such a 3 hour period was allowed between 16 galactose-biotin and radioactivity administration, the liver levels. were lower and comparable to that of the HSA-containing agent (approximately 1% injected dose/gram).

Experiments were. also carried out using I-125 labeled MAb-streptavidin conjugate and In-111 labeled DOTA-biotin to assess the relative stoichiometry of those materials at the tumor target site using 16 galactose-biotin as a clearing agent. Previous studies with (galactose)$_{35}$-HSA-(biotin)$_2$ had shown that an expected 4:1 ratio of DOTA-biotin to MAb-streptavidin (streptavidin has 4 biotin binding sites) could be achieved at the tumor with an optimized dose of that clearing agent. When a similar protocol was employed with the 16 galactose-biotin construct, the ratio of DOTA-biotin to MAb-streptavidin was only 2.65. This indicated that some filling of tumor-associated streptavidin may have occurred, although the nature of such blockage (16 galactose-biotin or biotin released therefrom) was undetermined. Experiments to assess the nature of this blockade are underway.

In summary, galactose cluster conjugates exhibited ability to clear circulating conjugate, provided the galactose cluster contains a sufficient number of appropriately spaced galactosyl residues. 16 Galactose-biotin has proven to be an effective construct for clearing MAb-streptavidin from the circulation (both vascular and extravascular spaces). Despite an apparent blockade of some pretargeted biotin binding sites at the tumor, efficient tumor targeting can still be achieved using this agent. Stabilization of the linkage between biotin and the galactose cluster may minimize any tumor-associated biotin binding site compromise by the galactose cluster-biotin construct.

EXAMPLE VII

Director Reagent Preparation

Figure 3:
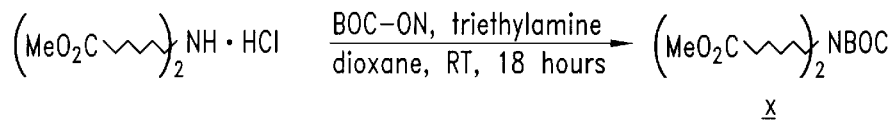
FIG. 3 schematically depicts the synthesis of an eight galactose-containing galactose cluster.
Figure 3:
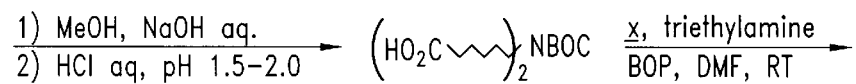
Figure 3:
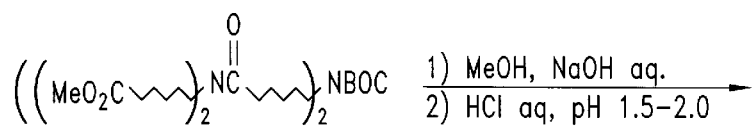
Figure 3:
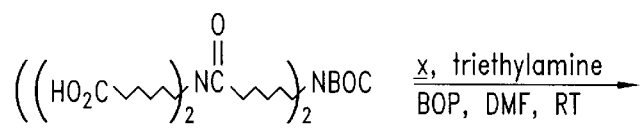
Figure 3:
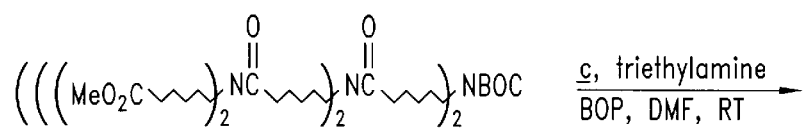
Figure 3:
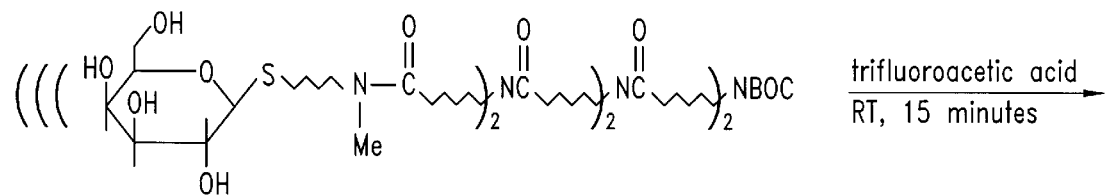
Figure 3:
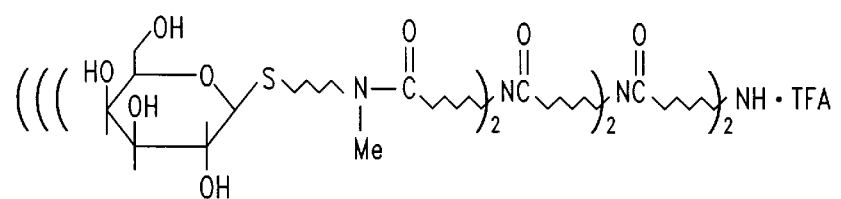

This procedure is schematically shown in FIG. 3.

N-BOC-Bis-methvlester. To 1.00 g (3.23 mmol) of the amine hydrochloride, N,N-bis-(6-methoxycarbonyl-hexyl) amine hydrochloride prepared as described above, was added 1.5 mL (10.6 mmol) of triethylamine followed by 875 mg (3.55 mmol, 1.1 equiv) of BOC-ON, 2-(tert-butoxycarbonyloxyimino)-2-phenylacetonitrile. The mixture was stirred at room temperature for 18 hours and then concentrated. The residue was diluted with 100 mL of ethyl acetate and washed with 1N aqueous hydrochloric acid (3×50 mL), followed by saturated aqueous sodium bicarbonate (2×mL). The organic phase was dried over magnesium sulfate, filtered and concentrated. The residue was chromatographed on silica gel, eluting with 15% (percentage based upon volume) ethyl acetate/hexane. Chromatographic fractions containing product were combined and concentrated to afford 990 mg of product as a near colorless oil (83%).

N-BOC-Bis-acid. To 980 mg (2.62 mmol) of the diester prepared in the previous step in 10 mL of methanol was added 5.8 mL of 1N aqueous sodium hydroxide (5.8 mmol). The mixture was stirred at room temperature for 16 hours and then concentrated. The residue was diluted with 30 mL of deionized water and acidified to pH 1.5–2. The mixture was extracted with ethyl acetate (6×50 mL). The organic extracts were dried over magnesium sulfate, filtered and concentrated. The residue was chromatographed on reverse phase C-18 silica gel commercially available from J. T. Baker, eluting with 65% methanol/water. Chromatographic fractions containing product were combined and concentrated to afford 851 mg of product as a near colorless oil (94%).

N-BOC-Tetra-methyl ester. To 825 mg (2.39 mmol) of the bis-acid prepared as described above in 35 mL of dry dimethylformamide, was added 1.75 g (5.65 mmol, 2.36 equiv) of amine hydrochloride, N,N-bis-(6-methoxycarbonylhexyl)amine hydrochloride, and 3.0 mL of triethylamine followed by 2.4 g (5.4 mmol, 2.3 equiv) of BOP. The mixture was stirred at room temperature for 17 hours and then concentrated. The residue was diluted with 100 mL of ethyl acetate and washed with 1N hydrochloric acid (3×50 mL) followed by washing with aqueous sodium bicarbonate (2×50 mL). The organic phase was dried over magnesium sulfate, filtered and concentrated. The residue was chromatographed on silica gel, eluting with ethyl acetate. Chromatographic fractions containing product were combined and concentrated to afford 1.63 g of the product as a near colorless oil (80%).

N-BOC-Tetra-acid. To a solution of 1.41 g (1.65 mmol) of tetra-methyl ester prepared as described above in 25 mL of methanol was added 7.4 mL (7.4 mmol) of 1N aqueous sodium hydroxide. The mixture was stirred at room temperature for 22 hours and then concentrated. The residue was diluted with 30 mL of deionized water and acidified to pH 2 with 1N aqueous hydrochloric acid. The mixture was extracted with 3:1 (ratio by volume) ethyl acetate/isopropanol (3×100 mL). The organic extracts were concentrated. The residue was chromatographed on reverse phase C-18 silica gel, eluting initially with 50:50 (ratio by volume) methanol/water and eventually with 75:25 methanol/water. Chromatographic fractions containing product were combined and concentrated to afford 1.19 g of the product as a colorless oil (90%).

N-BOC Octa-methyl ester. To a mixture of 501 mg (0.626 mmol) of tetra-acid prepared as described above and 30 mL of dry dimethylformamide was added 968 mg (3.12 mmol, 5.0 equiv) of amine hydrochloride, N,N'-bis-(6-methoxycarboxyhexyl)amine hydrochloride, and 2.0 mL (14.2 mmol) of triethylamine, followed by 1.22 g (2.76 mmol, 4.6 equiv) BOP. The mixture was stirred at room temperature for 19 hours and then concentrated. The residue was diluted with 75 mL of ethyl acetate and washed with 1N aqueous hydrochloric acid (2×50 mL). The organic.phase was dried over magnesium sulfate, filtered and concentrated. The residue was chromatographed on reverse phase C-18 silica gel, eluting initially with 60:40 methanol/water and eventually with 90:10 methanol/water. The chromatographic fractions containing product were combined and concentrated to afford 715 mg of the product as a colorless oil (63%).

N-BOC Octa-acid. To a solution of 715 mg (0.393 mmol) of octa-methyl ester prepared as described above in 20 mL of methanol was added 6 mL of 1N aqueous sodium hydroxide (6 mmol) and 5 mL of deionized water. The mixture was stirred at room temperature for 16 hours and then concentrated. The residue was diluted with 20 mL of deionized water, and the solution was acidified to pH 1.5–2.0. The mixture was concentrated, and the residue was chromatographed on reverse phase C-18 silica gel, eluting initially with 50:50 methanol/water and eventually with 80:20 methanol/water. The chromatographic fractions containing product were combined and concentrated to afford 647 mg of the product as a near colorless oil (96%).

The above procedure is designed for the formation of a galactose cluster of 8 galactose residues. The four galactose version could be made in accordance with this procedure by proceeding from the tetra acid to the galactose derivatization step, which is described below for the 8-galactose cluster. Similarly, 16, 32, etc. galactose cluster constructs can be prepared in accordance with the present invention by introduction of two more iterations of the methyl ester and acid formation steps. More specifically, the 16-methyl ester construct, the 16-acid, the 32-methyl ester and so on would be prepared essentially as described above for the tetra and octa forms. When the desired number of acid residues are formed, the galactose derivatization step is employed, with the proportions of the components adjusted to accommodate the number of acid residues.

N-BOC-Octa-galactosvl construct. To a mixture of 161 mg (94 mmol) of octa-acid prepared as described above and 225 mg (906 micromol, 9.64 equiv) of galactose amine, 4-N-methylaminobutyl-1-thio-beta-D-galactopyranoside, in 8 mL of dry dimethylformamide was added 0.5 mL (3.54 mmol) of triethylamine followed by 371 mg (839 micromol, 8.4 equiv) of BOP. The mixture was stirred at room temperature for 17 hours and then concentrated. The residue was chromatographed on reverse phase C-18 silica gel, eluting initially with 40:60 methanol/water and finally with 70:30 methanol/water. The chromatographic fractions containing product were combined and concentrated to afford 170 mg of the product as a near colorless oil (47%).

Octa-galactosyl amine. To 170 mg of the N-BOC-octa-galactosyl construct prepared as described above was added 5 mL of trifluoroacetic acid. The mixture was stirred at room temperature for 10 minutes and then concentrated. The residue was diluted with 10 mL of methanol and reconcentrated. The residue is used without further purification.

Other director reagent families bearing functional groups other than the amine group of the construct formed above can be made from the amine construct using standard chemical techniques conversion of amines to other functional groups.

EXAMPLE VIII

Extended Director Reagent Preparation
Extender-Galactose Cluster Preparation.

Figure 4:
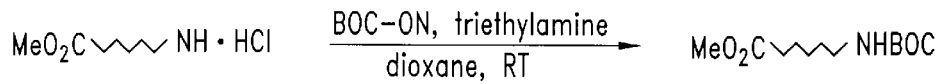
FIG. 4 schematically shows the synthesis of an extended eight galactose-containing galactose cluster.
Figure 4:
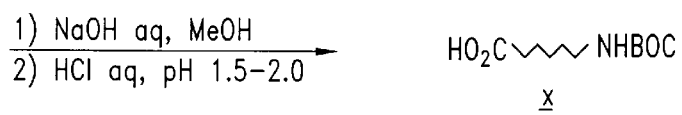
Figure 4:
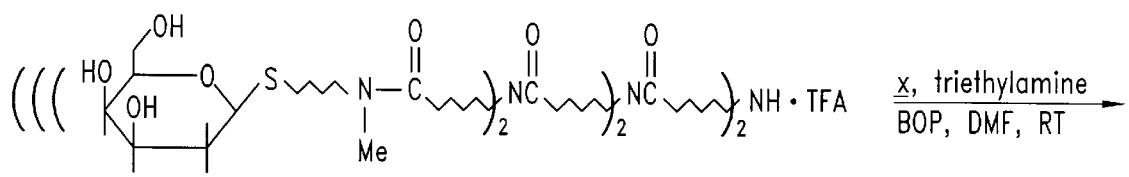
Figure 4:
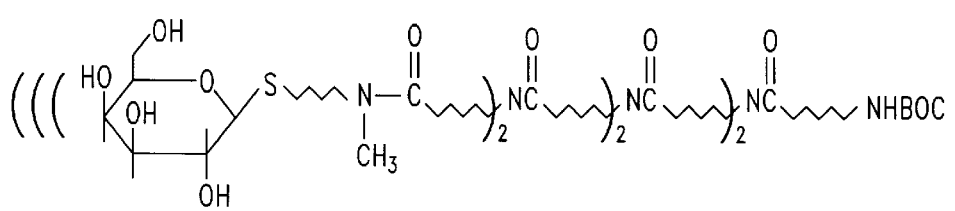
Figure 4:
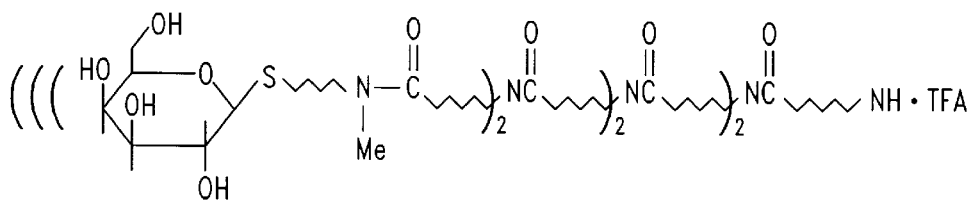

This procedure is schematically shown in FIG. 4. This procedure is undertaken, if necessary, to facilitate director reagent conjugation. The extension procedure, which in this example preserves an amine functional group, can also be used to introduce an alternative functional group as discussed herein.

Methyl 6-(N-BOC)-aminocaoroate. To a mixture of amine hydrochloride, methyl-6-aminohexanoate hydrochloride, prepared as described above is added 1.1 equivalents of BOC-ON followed by 2–3 equivalents of triethylamine. The mixture is stirred at 15–30° C. for 16–24 hours and the concentrated. The residue is dissolved in ethyl acetate and washed with 1N aqueous hydrochloric acid and then with saturated aqueous sodium bicarbonate. The organic phase is dried over magnesium sulfate, filtered and concentrated via reduced pressure rotary evaporation. The residue is chromatographed on silica gel, eluting with 25% ethyl acetate/hexane. The chromatographic fractions containing the product are combined and concentrated to afford the product.

6-(N-BOC)-aminocaproic acid. To a solution of the methyl ester, methyl 6-(N-BOC)-aminocaproate, in methanol is added 1.5 equivalents of 1N aqueous sodium hydroxide. The mixture is stirred at 15–30° C. for 16–24 hours and then concentrated. The residue is diluted with deionized water and extracted with ethyl acetate. The organic extracts are combined, dried over magnesium sulfate, filtered and concentrated. The residue is chromatographed on silica gel, eluting initially with 25% ethyl acetate/hexane and finally with 100% ethyl acetate. The chromatographic fractions containing the product are combined and concentrated to afford the product.

N-BOC extended octa-galactosyl construct. To a solution of the octa-galactosyl amine prepared as described above in dimethylformamide and 1.5–3 equivalents of 6-(N-BOC)-aminocaproic acid is added 4–6 equivalents of triethylamine followed by 1.1–1.5 equivalents of BOP. The mixture is stirred at 15–30° C. for 4–24 hours and then concentrated. The residue is diluted with deionized water, and the pH is adjusted to 1.5–2.0 by addition of 1N aqueous hydrochloric acid. The mixture is washed with ethyl acetate. The aqueous phase is concentrated, and the residue is chromatographed on reverse phase C-18 silica gel, eluting initially with 50:50 methanol/water and finally with 65:35 methanol/water. The chromatographic fractions containing product are combined and concentrated to afford the product.

Amine extended octa-galactosvl construct. To the N-BOC protected amine prepared in the previous step is added trifluoroacetic acid. The mixture is stirred at 15–30° C. for 10 minutes and then concentrated. The residue is diluted with methanol and reconcentrated to afford the product which is used without further purification.

EXAMPLE IX

Radiolabeled Annexin-Galactose Cluster Conjugates
Trifunctional Linker Approach

A. Chelate Preparation.

Figure 5:
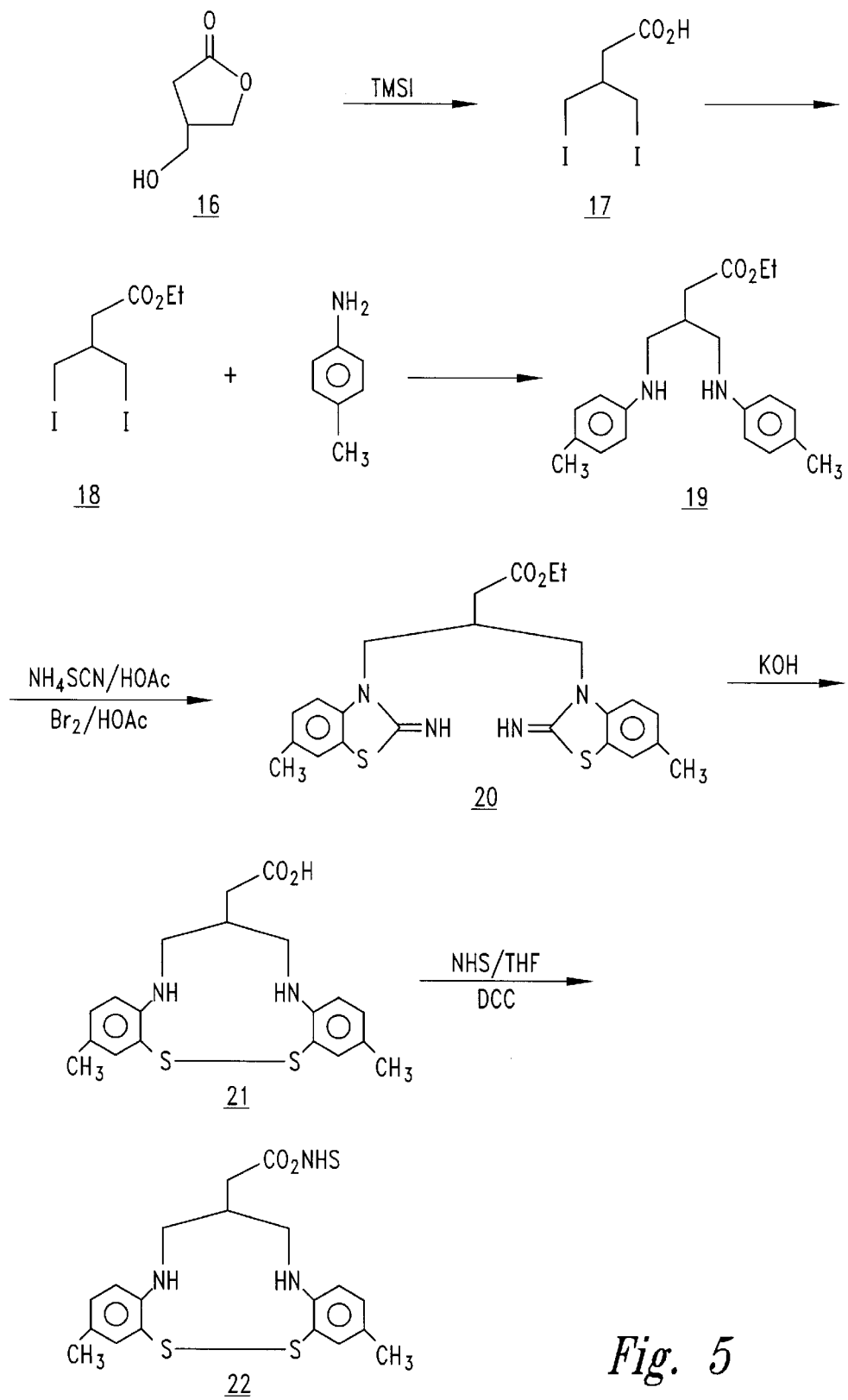
FIG. 5 schematically shows the synthesis of N,N'-bis (disulfidyl-4-methylphenyl) -gamma, gamma'-diamino-isovalerate N-hydroxysuccinimide.

Production of chelate N,N'-bis(2-disulfidyl-4-methylphenyl)-gamma,gamma'-diamino-isovalerate N-hydroxysuccinimide, as shown schematically in FIG. 5.

3-Iodomethyl-4-iodobutyric acid: To a solution of 1.61 g (10 mmole) 3-hydroxymethyl-4-butanolide (prepared by the procedure of Kinoshita and Hirano, *J. Hetrocyclic Chem.*, 29: 1025, 1992) in 100 mL carbon tetrachloride is added 8 g (40 mmole) of iodotrimethylsilane. The reaction mixture is heated at 50° C. for 12 hours under nitrogen. The mixture is diluted with chloroform and washed with water (3×100 mL), 5% aqueous sodium thiosulfate (100 mL), 10% aqueous sodium bicarbonate and brine. The organic layer is dried over magnesium sulfate, filtered and evaporated to give the desired crude product. The crude product is purified by silica gel chromatography (ethyl acetate-hexane=3:7 as the eluting solvent) to give 3-iodomethyl-4-iodobutyric acid.

Ethyl-3-iodomethyl-4-iodobutyrate: A solution of 2.831 g (8 mmole) 3-iodomethyl-4-iodobutyric acid in 80 mL ethanol is saturated with HCl gas at 0° C. After stirring the solution at room temperature for two days, the solvent is removed under vacuum, and the residue is dissolved in dichloromethane. The dichloromethane layer is washed with 10% aqueous sodium bicarbonate (3×100 mL), water (1×100 mL) and brine. The separated dichloromethane layer is dried over with magnesium sulfate, filtered and evaporated to give ethyl-3-iodomethyl-4-iodobutyrate.

Ethyl-qamma, gamma'-di(4-methylanilino) isovalerate: A stirred solution of 7.5 g (70 mmole) 4-toluidine, 2.764 g (7 mmole) ethyl-3-iodomethyl-4-iodobutyrate and 0.588 g (7 mmole) sodium bicarbonate in 30 mL dry dimethyl sulfoxide is heated at 100° C. for 3 hours under nitrogen. The cooled mixture is poured onto 400 mL ice water with stirring. The resulting precipitate is collected by filtration.

The remaining 4-toluidine in the precipitate is removed by washing with aqueous acetic acid several times. The product is obtained by recrystallization of the washed precipitate in heptane.

Ethyl-gamma,gamma'-[1,3-di(2-imino-6-methyl benzthiazolvl-3)]isovalerate: To a magnetically stirred suspension of 2.0 g (6.5 mmole) ethyl-gamma,gamma'-di(4-methylanilino)isovalerate in 250 mL glacial acetic acid is added ammonium thiocyanate (3.5 g, 0.046 mole) followed by the dropwise addition of a solution of bromine (7.27 g, 0.046 mole) in 50 mL glacial acetic acid. After addition is complete, stirring is continued overnight. The yellow precipitate of dihydrobromide salt is filtered and dried. The dried solid is then dissolved in hot water and the benzothiazole free base is liberated with saturated sodium bicarbonate solution. The white solid is filtered and dried to give crude product which is used without further purification.

N,N'-Bis(2-disulfidyl-4-methylphenyl)-gamma, gamma'-diaminoisovalerate aid: To a suspension of ethyl-gamma, gamma'-[1,3-di(2-imino-6-methyl benzthiazolyl-3)] isovalerate in 40 mL distilled water, solid potassium hydroxide pellets (20.0 g, 0.037 mole) are added, and the resulting solution is heated at 120° C. for 15–24 hours. After several hours of heating, the suspension becomes a clear solution. The reaction mixture is cooled in an ice bath and acidified with 5.0N acetic acid to pH 5.0, and the aqueous solution is extracted with three 100 mL portions of ethyl acetate. The combined ethyl acetate extracts are dried over anhydrous sodium sulfate and filtered. Solvent from the filtrate is removed under reduced pressure to give crude product. This crude product is chromatographed on silica gel column using a 20:80 mixture of ethyl acetate:hexane with 1% acetic acid as eluting solvent to give the product as a crystalline yellow solid.

N,N'-Bis(2-disulfidyl-4-methylphenyl)-gamma, gamma'-diaminosiovalerate N-hydroxvsuccinimide: N,N'-Bis(2-disulfidyl-4-methylphenyl)-gamma,gamma'-diamino-isovaleric acid is reacted with N-hydroxysuccinimide (NHS) and dicyclohexylcarbodiimide (DCC) in either tetrahydrofuran (THF) or dimethylformamide (DMF) at room temperature. After stirring overnight at room temperature, the solvent is removed, and the crude product is purified by column chromatography on silica gel.

B. Conjugate Formation.

This chelate is amenable to use with a suitable trifunctional linker to form a radiolabeled annexin-galactose cluster conjugate of the present invention as described below.

Commercially available N-epsilon-t-BOC-lysine (Sigma Chemical Company) is converted, using trifluoroacetic anhydride, to its N-alpha-trifluoroacetamide adduct. Activation of the carboxylic acid functionality, for example with BOP (benzotriazol-1-yloxy-tris(dimethyl-amino)-phosphonium hexafluorophosphate) commercially available from Aldrich Chemical Company, and reaction of the activated moiety with the single available amine on a galactose cluster, e.g., formed as described above, affords a galactose cluster-trifunctional linker species. The alpha-amine of lysine trifunctional linker component of the galactose clustertrifunctional linker species is deblocked using methanolic sodium hydroxide. Reaction with the N-hydroxysuccinimide ester of the chelate molecule formed as set forth in part A of this example affords a galactose cluster-chelate-trifunctional linker species. Deprotection of the epsilon amine of the lysine trifunctional linker component using trifluoroacetic acid, followed by reaction with succinic anhydride provides an available carboxylic acid functionality through which the annexin may be conjugated following activation of the carboxylic acid (e.cr, with BOP).

Kits containing one or more of the components described above are also contemplated. For instance, galactose cluster-biotin conjugate may be provided in a sterile container for use in pretargeting procedures. Alternatively, such a galactose cluster-biotin conjugate may be vialed in a non-sterile condition for use as a research reagent.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An improved method of therapy which comprises the administration of a compound comprising a binding moiety, targeting moiety or active agent, which is selectively delivered to a target sites, wherein the improvement comprises the addition of a reagent which provides for hepatic-directed clearance, wherein the reagent includes:

a hexose cluster characterized by at least nine hexose residues connected in an iteratively branched configuration, each branch of the configuration having three prongs, and a functional moiety through which the binding moiety, targeting moiety or active agent is directly or indirectly bound.

2. The method of claim 1, wherein the hexose cluster is formed of N-acetylgalactosamine residues.

3. The method of claim 1, wherein the functional moiety is selected from the group consisting of: activated esters, maleimides, isocyanates, alkyl halides, hydrazides, thiols, imidates, and aldehydes.

4. An improved method of therapy which comprises the administration of a compound comprising a binding moiety, targeting moiety or active agent, which is selectively delivered to a target site, wherein the improvement comprises the addition of a reagent which provides for hepatic clearance, wherein the reagent includes:

(a) a galactose cluster having a formula selected from the group consisting of

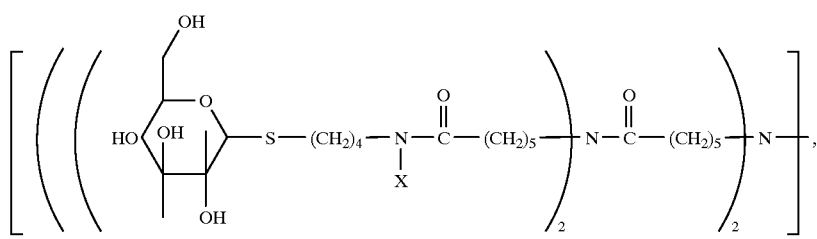

-continued

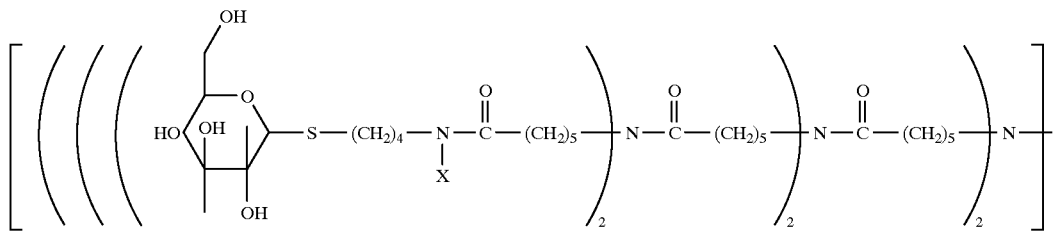

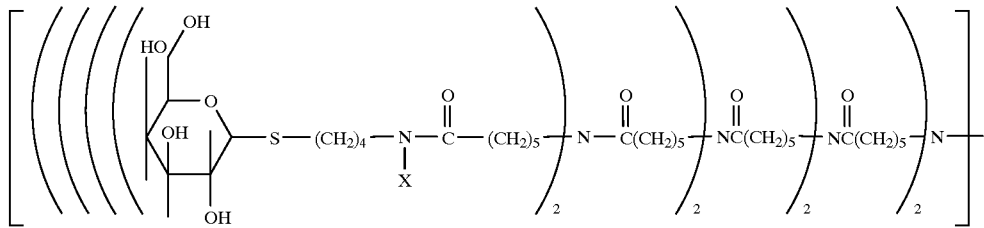

and

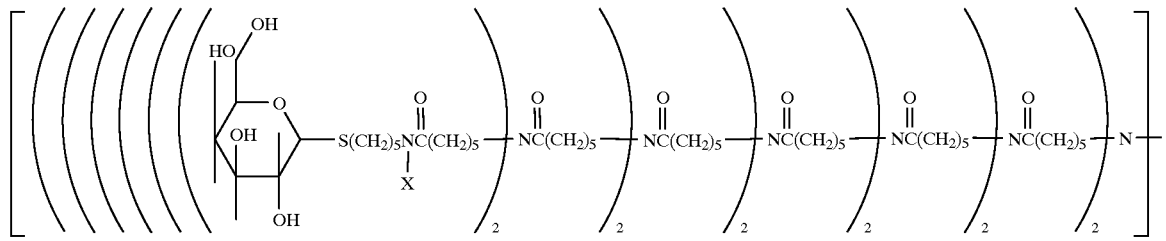

wherein X is H or methyl; and (b) a functional moiety through which the binding moiety, targeting moiety or active agent is directly or indirectly bound.

5. An improved method of therapy which comprises the administration of a compound comprising a binding moiety, targeting moiety or active agent, which is selectively delivered to a target site, wherein the improvement comprises the addition of a reagent which provides for hepatic clearance, wherein the reagent includes:

(a) a galactose cluster having a formula selected from the group consisting of

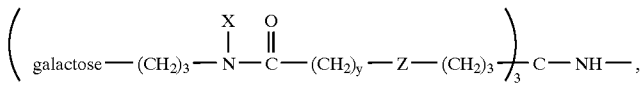

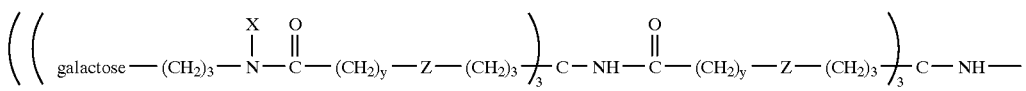

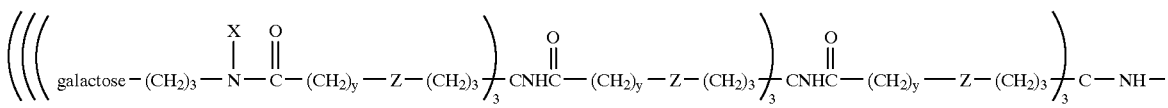

wherein X is H or methyl, y is from 1 to 10, and Z is O or S; and (b) a functional moiety through which the binding moiety, targeting moiety or active agent is directly or indirectly bound.

* * * * *